US010842556B1

(12) United States Patent
Tandri et al.

(10) Patent No.: US 10,842,556 B1
(45) Date of Patent: Nov. 24, 2020

(54) METHOD AND APPARATUS TO TREAT CARDIOPULMONARY DISEASE

(71) Applicants: THE JOHNS HOPKINS UNIVERSITY, Baltimore, MD (US); CORIDEA LLC, New York, NY (US)

(72) Inventors: Harikrishna Tandri, Ellicott City, MD (US); Mark Gelfand, New York, NY (US); Tamara Colette Baynham, Powie, MD (US); Zoar Engelman, New York, NY (US)

(73) Assignees: The Johns Hopkins University, Baltimore, MD (US); Coridea, LLC, New York, NY (US)

( * ) Notice: Subject to any disclaimer, the term of this patent is extended or adjusted under 35 U.S.C. 154(b) by 1105 days.

(21) Appl. No.: 15/152,048

(22) Filed: May 11, 2016

Related U.S. Application Data

(60) Provisional application No. 62/162,615, filed on May 15, 2015.

(51) Int. Cl.
*A61B 18/14* (2006.01)
*A61B 18/00* (2006.01)

(52) U.S. Cl.
CPC . *A61B 18/1492* (2013.01); *A61B 2018/00011* (2013.01); *A61B 2018/00345* (2013.01);
(Continued)

(58) Field of Classification Search
CPC .. A61B 2018/00434; A61B 2018/1425; A61B 18/1492; A61B 2018/00982;
(Continued)

(56) References Cited

U.S. PATENT DOCUMENTS 7,725,188 B2   5/2010   Errico et al.
7,966,076 B2   6/2011   Westlund et al.
(Continued)

FOREIGN PATENT DOCUMENTS

WO   2011127216 A2   10/2011
WO   2012177551 A1   12/2012

OTHER PUBLICATIONS

Gibbons et al. (2011) Neuromodulation targets intrinsic cardiac neurons to attenuate neuronally mediated atrial arrhythmias. Am J Physiol Regul Integr Comp Physiol 302: R357-R364.
(Continued)

*Primary Examiner* — Joseph A Stoklosa
*Assistant Examiner* — Sean W Collins
(74) *Attorney, Agent, or Firm* — DLA Piper LLP (US)

(57) ABSTRACT

Methods and devices for treating patients having cardiopulmonary disease such as cardiac arrhythmias, ventricular arrhythmias, pulmonary hypertension, or heart failure comprising a tracheal approach. The method includes ablating a deep cardiac plexus of a patient by advancing an treatment apparatus into a trachea of the patient, extending an ablative energy delivery element of the treatment apparatus through a wall of the trachea at a level of the trachea proximate a tracheal bifurcation, positioning the ablative energy delivery element at a target space between the trachea, an aorta and a pulmonary artery, and ablating, by the ablative energy delivery element, tissue within the target space to substantially disable the deep cardiac plexus.

37 Claims, 11 Drawing Sheets

(52) U.S. Cl.
CPC ........... *A61B 2018/00434* (2013.01); *A61B 2018/00577* (2013.01); *A61B 2018/00839* (2013.01); *A61B 2018/00982* (2013.01)

(58) Field of Classification Search
CPC A61B 2018/00839; A61B 2018/00577; A61B 2018/00345; A61B 2018/00011
See application file for complete search history.

(56) References Cited

U.S. PATENT DOCUMENTS

| | | | |
|---|---|---|---|
| 8,301,239 B2 | 10/2012 | Libbus et al. | |
| 2005/0224086 A1* | 10/2005 | Nahon | A61B 18/02 128/899 |
| 2008/0228252 A1* | 9/2008 | Westlund | A61N 1/0553 607/130 |
| 2012/0209257 A1* | 8/2012 | van der Weide | A61B 18/1815 606/23 |
| 2013/0204068 A1* | 8/2013 | Gnanashanmugam | A61N 5/1002 600/1 |
| 2013/0317339 A1* | 11/2013 | Waldstreicher | A61B 8/12 600/409 |
| 2015/0065945 A1* | 3/2015 | Zarins | A61B 18/1492 604/21 |

OTHER PUBLICATIONS

Pinho-Gomes et al. (2014) Surgical treatment of atrial fibrillation: an updated review. European Journal of Cardio-Thoracic Surgery 46: 167-178.

Qi et al. (2014) Nav1.8 channels in ganglionated pleximodulate atrial fibrillation inducibility. Cardiovascular Research 102: 480-486.

Quintana et al. (2014) Left Atrial Anatomy Relevant to Catheter Ablation. Cardiology Research and Practice: 1-17.

\* cited by examiner

METHOD AND APPARATUS TO TREAT CARDIOPULMONARY DISEASE

CROSS REFERENCE TO RELATED APPLICATIONS

This application claims priority to the following U.S. Provisional Applications, the disclosures of which are incorporated by reference herein in their entireties: U.S. Prov. App. No. 62/162,615, filed May 15, 2015.

FIELD OF THE INVENTION

The invention relates generally to medical devices and more specifically to a methods and devices for cardiopulmonary denervation.

BACKGROUND

Cardiopulmonary diseases have a serious effect on quality of life and affect a growing population around the world. Some cardiopulmonary diseases may be treatable by modulating nerve activity associated with the heart, lungs or their vasculature. Inhibiting or eliminating nerve signals by ablating or blocking the cardiac plexus may have therapeutic benefits for cardiopulmonary diseases such as pulmonary artery hypertension, heart failure, or ventricular arrhythmia.

Cardiac arrhythmias (CA) including ventricular arrhythmias (VA) are a leading cause of sudden cardiac arrest, and account for approximately 400,000 deaths annually in the United States alone. CA is common in advanced structural heart disease and is an important cause of morbidity and mortality. Abnormalities in cardiac impulse generation and propagation underlie the genesis of CA in structural heart disease and CA is frequently encountered in patients who sustain a myocardial infarction and adversely affects prognosis. The burden of CA is rising mainly due to a rise in incidence of coronary artery disease and secondarily due to improved survival after myocardial infarction. High-risk subjects for CA are identified by rigorous screening and receive implantable cardioverter defibrillator (ICD) therapy. Although ICD protects them against sudden cardiac arrest, recurrent CA occur during the natural history of structural and electrical remodeling and the management of this is challenging. Also the worldwide prevalence of coronary artery disease (CAD) is on the rise and CA follows this paradigm. As such it is estimated that the societal and economic burden of CA will rise significantly over the next decade.

Current therapies to treat CA are largely ineffective. Therapeutic options for the treatment of these CA include antiarrhythmic drugs, implantable cardioverter defibrillators (ICDs), and surgical and catheter ablations. Antiarrhythmic drugs have disappointing efficacy and adverse side effects that may outweigh the benefits. ICDs effectively terminate VT/VF episodes and represent the mainstay therapy to prevent sudden death. ICD prolongs survival in patients with CA but does not solve the underlying problem. ICD shocks are painful, reduce the quality of life, and predict increased risk of death and heart failure. Radiofrequency catheter ablation is an important treatment option for patients with monomorphic ventricular arrhythmias. This procedure that is modestly effective in experienced hands, carries significant risk, and is quite expensive. Currently over 10,000 catheter ablation procedures are performed for CA in the US and >40% of them will fail in less than 6 months. With each procedure costing over $20,000, the economic impact of CA management is approximately $200 M in the United States alone. Multiple catheter ablations are fairly common among patients with advanced disease, but the results of repeat ablation are not any better.

The sympathetic nervous system plays an important role in genesis and maintenance of CA. Sympathetic blockade is a well-accepted therapy for ventricular arrhythmias. Current approaches to achieve this include drug therapies such as beta-blockers that act at receptor level, surgical BCSD at the level of the sympathetic chain ganglia, thoracic epidural anesthesia at the spinal cord level or general anesthesia, which acts at the cortical level. Beta-blockers are the cornerstone of CA management and are used universally to treat CA in conjunction with other therapies. Thoracic epidural anesthesia to block sympathetic nerves has been shown to be effective in terminating refractory CA during electrical storms. Left cardiac sympathetic denervation (LCSD) has been shown to be effective in treatment of refractory arrhythmias in advanced structural heart disease despite failure of drug therapy and catheter ablation. LCSD is an accepted treatment for preventing recurrent VF in Long QT syndrome and in patients with catecholaminergic polymorphic ventricular tachycardia (CPVT). Recently bilateral cardiac sympathetic denervation (BCSD) has been shown to be more effective in preventing CA recurrence compared to LCSD.

Sympathetic denervation by BCSD achieves arrhythmia control in >70% of with refractory VA patients, yet surgical cardiac denervation is grossly underutilized. The main reason for this is BCSD is invasive and is complicated. The procedure involves video-assisted thoracoscopic resection of the stellate and the first 4 thoracic sympathetic ganglia performed by an experienced surgeon using single lung ventilation. Patients with severe heart disease do not tolerate the surgery and prior cardiac surgery complicates the procedure due to intrathoracic adhesions. To be effective surgical sympathetic denervation has to be performed bilaterally using single lung ventilation on the contralateral side during the surgical resection. Thus, there is a need for a minimally invasive device and method of use to achieve bilateral complete cardiac sympathetic denervation through disruption of the deep cardiac plexus.

Pulmonary hypertension (PH) is a progressive disorder characterized by abnormally high blood pressure (hypertension) in the pulmonary artery, the blood vessel that carries blood from the heart to the lungs. Pulmonary hypertension occurs when most of the very small arteries throughout the lungs narrow in diameter, which increases the resistance to blood flow through the lungs. This is known as pulmonary vascular resistance. To overcome the increased resistance, blood pressure increases in the pulmonary artery and in the right ventricle of the heart, which is the chamber that pumps blood into the pulmonary artery. Ultimately, the increased blood pressure can damage the right ventricle of the heart. The heart may become so weak that it can't pump enough blood to the lungs, which can lead to heart failure (HF). HF is the most common cause of death in people who have PH.

Signs and symptoms of PH occur when increased blood pressure cannot fully overcome the elevated resistance. As a result, the flow of oxygenated blood from the lungs to the rest of the body is insufficient. Shortness of breath (dyspnea) during exertion and fainting spells are the most common symptoms of pulmonary hypertension. People with this disorder may experience additional symptoms, particularly as the condition worsens. Other symptoms include dizziness, swelling (edema) of the ankles or legs, chest pain, and a rapid heart rate.

The World Health Organization divides pulmonary hypertension (PH) into five groups. These groups are organized based on the cause of the condition. In all groups, the average pressure in the pulmonary arteries is higher than 25 mmHg at rest or 30 mmHg during physical activity. The pressure in normal pulmonary arteries is 8-20 mmHg at rest. Group 1 is called pulmonary artery hypertension and groups 2 through 5 are called pulmonary hypertension. However, together all groups are called pulmonary hypertension. Group 1 pulmonary artery hypertension (PAH) includes the following: idiopathic (no known cause) PAH, inherited PAH, PAH caused by drugs or toxins, PAH caused by conditions that affect the veins and small blood vessels of the lungs, and PAH caused by conditions such as connective tissue disease, HIV infection, liver disease, congenital heart disease, sickle cell disease, and schistosomiasis (infection caused by a parasite). Group 2 includes PH with left heart disease. Conditions that affect the left side of the heart, such as mitral valve disease or long-term high blood pressure, can cause left heart disease and PH. Group 3 includes PH associated with lung diseases, such as chronic obstructive pulmonary disease (COPD) and interstitial lung diseases. Interstitial lung diseases cause scarring of the lung tissue. Group 3 also includes PH associated with sleep-related disorders, such as sleep apnea. Group 4 includes PH caused by blood clots in the lungs or blood clotting disorders. Group 5 includes PH caused by various other diseases or condition including: blood disorders, such as polycythemia vera and essential thromocythemia; systemic disorders, such as sarcoidosis and vasculitis; metabolic disorders, such as thyroid disease and glycogen storage disease; and other conditions such as tumors that press on the pulmonary arteries or kidney disease.

Exercise testing is used to determine the severity of PH. This testing consists of either a 6-minute walk test or a cardiopulmonary exercise test. A 6-minute walk test measures the distance you can quickly walk in 6 minutes. A cardiopulmonary exercise test measures how well your lungs and heart work while you exercise on a treadmill or bicycle. The activity level is linked to the severity of PH. The rating system ranges from class 1 to class 4. Class 1 has no limitations in performance of regular physical activities, such as walking or climbing stairs. Class 2 has slight or mild limitations. Class 3 has marked or noticeable limits. Class 4 denotes severe limitations in performing regular physical activity.

PH is a progressive and irreversible disorder that may eventually result in right ventricular failure and death. Despite advances in the treatment of PH, the overall prognosis remains poor with an approximate annual mortality rate of 11.8% in patients with idiopathic PAH (IPAH). Heart-lung transplantation and bilateral lung transplantation remain the final option for patients with PH remaining in New York Heart Association (NYHA) functional class III/IV despite combination therapy. While initial symptoms of PH are non-specific, including dyspnea and fatigue following physical exertion, these often progress to occur with minimal exertion or, in extreme cases at rest. Additionally, patients often experience swelling in the ankles or legs (edema); bluish lips and skin (cyanosis); chest pain; and palpitations. Such debilitating symptoms result in substantial impairments in patients' Health-Related Quality of Life (HRQoL). In particular, PH results in significant impairment of physical functioning, ability to perform activities of daily living and social functioning, and many patients experience feelings of depression and anxiety and difficulty sleeping.

PH has no cure, however; treatment may help relieve symptoms and slow the progression of the disease. Treatment is dependent on the type of PH as well as the severity. PH treatments include medications as well as interventional and surgical procedures. Medicines include phosphodiesterase-5 inhibitors (sildenafil), prostanoids (such as epopstenol), endothelin receptor antagonists, calcium channel blockers (such as diltiazem), diuretics, blood-thinning medications, and digoxin. Medications have been associated with mild-to-moderate improvements in clinical symptoms, functional capacity, hemodynamics, and clinical outcomes. However, the severe side effects limit the use of these medications. Additionally, costs of these medications can be prohibitive, (e.g., prostanoids costs, ~$90,000/year). Oxygen therapy is also used to help raise the level of oxygen in the blood. Interventional techniques may palliate symptoms or serve as a bridge to transplantation in some patient with PH. Examples of interventional techniques include atrial septostomy and pulmonary artery denervation, which involves ablation of nerves attached to the outside surface of the pulmonary artery and innervating the lung.

Atrial septostomy (AS) is indicated in some patients with RV failure and associated PH in whom medical therapy has failed. Severe IPAH has been the main indication for AS, but other common indications include PAH associated with congenitally corrected heart disease, connective tissue disease, and distal chronic thromboembolic PH. The creation of the interatrial opening may be achieved by balloon AS, whereby an inflated balloon is forcefully pulled across the foramen ovale to tear the atrial septum and promote interatrial mixing of blood. As an alternative to balloon AS, balloon-dilated AS was developed in which the atrial septum is punctured using a needle, and the interatrial opening is progressively dilated with increasing balloon size. After balloon-dilated AS, the interatrial opening commonly closes, but repeated procedures can be performed with varying degrees of success. Fenestrated devices (or modified stent fenestration) have also been used to control the degree of shunt created and to maintain the patency of the interatrial opening. Procedural complications include balloon rupture and embolization of the balloon fragments, cardiac perforation or damage including rupture of the atrial appendage, failure to deflate the balloon, stroke and vascular complications. Patients with severe RV heart failure and extremely high pulmonary pressures do not tolerate AS because massive right-to-left shunting may result in severe systemic arterial oxygen desaturation and hypoxia leading to ischemia and death. Immediate mortality rates after AS vary from 0%-20%, with 30-day mortality rates as high as 23%.

Pulmonary artery denervation (PADN) is a technique that is thought to work by reducing sympathetic stimulation of the pulmonary vasculature. Autonomic regulation of pulmonary vascular tone is well recognized, however, its role in PH is less clearly defined. Increased plasma norepinephrine, muscle sympathetic nerve activity, and vessel sympathetic nerve endings have been demonstrated in patients with IPAH. Thus, the neurohormonal axis has been identified as a potential therapeutic target. Baroreceptors and sympathetic nerve fibers are localized in or near the bifurcation area of the main pulmonary artery (PA). PADN is technique that involves catheter ablation of nerves located at the bifurcation of the main PA and at the ostia of the right and left PA. When compared to medications, PADN results in improvement in both functional and clinical outcomes. However, PADN is associated with damage to the PA as well as an increased risk of thrombus formation. Additionally, the procedure requires significant skill and there is no acute measure of success for the procedure.

In view of the foregoing, it would be desirable to provide an apparatus and method to affect the neurohormonal axis in the treatment of patients having moderate to severe cardiopulmonary disease such as pulmonary hypertension, dyspnea, heart failure and cardiac arrhythmia. Desired aspects of the apparatus and method include improved clinical and functional outcomes, for example reduced dyspnea and improved exercise tolerance, as well as reduced vascular injury and thrombus formation.

SUMMARY OF DISCLOSURE

The inventors have conceived and disclose here a method of treating cardiopulmonary disease such as cardiac arrhythmias, ventricular arrhythmias, pulmonary hypertension, or heart failure and an apparatus comprising a tracheal approach, which may achieve bilateral denervation in a single zone taking advantage of the unique anatomy of the deep cardiac plexus where sympathetic nerves from both ganglia converge before entering the heart alongside the great vessels.

Therapies directed at cardiac efferent nerves that connect the sympathetic chain to the heart are complicated because of the anatomic constraints that prevented surgical access to the deep cardiac plexus. A proposed method of treatment comprises modulating the deep cardiac plexus with a device located in the nearby trachea. A bronchoscope may be a suitable delivery tool for a tracheal-based device. In order to facilitate procedural ease and adoption of this particular type of embodiment by electrophysiologists, who are typically not trained in the art of bronchoscopy, an embodiment may comprise a tracheal device incorporating technology that electrophysiologists are comfortable with and are typically found in electrophysiology labs, such as duplex ultrasound, Doppler ultrasound and fluoroscopy.

The present invention, in at least one embodiment, is directed to a method of treatment for patients with moderate to severe PH by ablating the sympathetic nerves that innervate the cardiac muscle and pulmonary arterial beds. The present disclosure describes methods to access the nerves through the trachea and modulate the function of one or more cardiac or pulmonary nerves to treat PH by providing for reduced dyspnea and improvement in exercise capacity leading to improvements in HRQoL.

Cardiac and pulmonary arterial beds are innervated by sympathetic nerves. These nerves arise from the stellate and upper thoracic ganglia and form a superficial as well as a deep cardiac plexus which is located behind the heart. Stimulation of these nerves causes an increase in catecholaminergic responses such as tachycardia, increased force of contraction, and pulmonary vasoconstriction. Stimulation also results in increased cardiac excitability and cardiac arrhythmias.

The vascular tone of the walls of pulmonary vessels are in part controlled by sympathetic stimulation by the sympathetic ganglia via the pulmonary nerves. These pulmonary nerves arise in the cervical and thoracic sympathetic ganglia and form a plexus called the deep cardiac plexus, which is anterior to the tracheal bifurcation. Electrical stimulation of these nerves results in increase in pulmonary arterial pressure. Conversely, blocking these nerves causes lowering of the pulmonary arterial blood pressure. The present method and apparatus exploits the unique anatomy of the deep cardiac plexus to easily access, ablate and achieve permanent disruption of bilateral pulmonary nerves to achieve reduction in pulmonary arterial pressure for patients having pulmonary hypertension. The apparatus in one embodiment may include a reusable ultrasound probe and associated workstation and a single-use mapping (i.e. electric stimulation) and ablation catheter.

Some embodiments are directed at suppressing the activity of target nerves. The target nerves include at least one sympathetic nerve or nerve fiber innervating the deep cardiac plexus. Suppression of nerve activity may occur by one or more of the following mechanisms: nerve ablation, irreversible electroporation, necrosis, apoptosis, altering gene expression, alteration of cytokine regulation. Suppression of the target nerve activity may result in pulmonary vasodilation. Pulmonary vasodilation provides for reduced pulmonary artery pressure, which may improve the health status of a PH patient.

Some embodiments are directed to a system capable of performing a procedure to suppress activity of a target neural structure of a patient and a method of using the system. An example of such a system may include a treatment apparatus configured to be advanced into the patient and an ablation energy generation system configured to be coupled to the treatment apparatus. The treatment apparatus may comprise an ablation device configured to modulate the activity of the target neural structure, an airway device for positioning the ablation device in proximity to the nerve target. The ablation generation system may generate and control delivery of ablation energy. Examples of ablation energy may include the following energy types: radiofrequency electrical current (e.g., monopolar, bipolar or other forms); therapeutic ultrasound (e.g., high intensity focused, unfocused directed or other forms); microwave; light; heat; phototherapy; magnetic; electrical; electromagnetic; cryogenic and chemical. The treatment apparatus advanced into the body of the patient may include a catheter. The treatment apparatus may be advanced into the body through the nose or mouth and into the trachea. Positioning of the treatment apparatus in proximity to the nerve target may be facilitated by the use of a visualization system. The treatment apparatus may comprise ablation elements to facilitate emission of ablative energy. An example of an ablation element includes electrically conductive electrodes configured to deliver radiofrequency electrical current and create a thermal ablation of tissue.

Some embodiments are directed to methods for treatment of a cardiopulmonary disease such as PH, heart failure, arrhythmia, or dyspnea. A method may include advancing a apparatus into the body of the patient; positioning the treatment apparatus in proximity to the target nerve; identifying the target nerve; delivering nerve suppression therapy; confirming suppression of the target nerve activity; and confirming technical and/or clinical success of the treatment. A method of treatment may further comprise steps of identifying non-target structures at risk of iatrogenic injury (e.g., using imaging technology, stimulation or blocking), securing the treatment apparatus, aiming ablation energy toward the target space, non-permanent confirmation of safety and effectiveness of prior to ablation, containing ablation energy in the target space, or confirmation of safety or effectiveness following ablation.

In some embodiments, a treatment apparatus is advanced into the body through the patient's airway to a target location in close proximity to a tracheal bifurcation of the patient and an element of the treatment apparatus is deployed to penetrate the wall of the trachea to enter a space that is anterior or inferior to the tracheal bifurcation to deliver treatment to target nerves.

In some embodiments, the ablation generation system may be configured to emit a substance or substances to suppress nerve activity. For example, emitted substances may include saline, ethanol, botulinum toxin or other neurotoxins, anesthetic agents, or other agents capable of suppressing nerve signal transmission. An ablation generation system configured to emit a substance may comprise a reservoir or some type of container for the substance; a pump, syringe or another mechanism to emit the substance; and a channel within the treatment apparatus to facilitate delivery of the substance to the target nerve.

These and other embodiments are described in greater detail below, in reference to the attached drawings.

DETAILED DESCRIPTION

Figure 1:
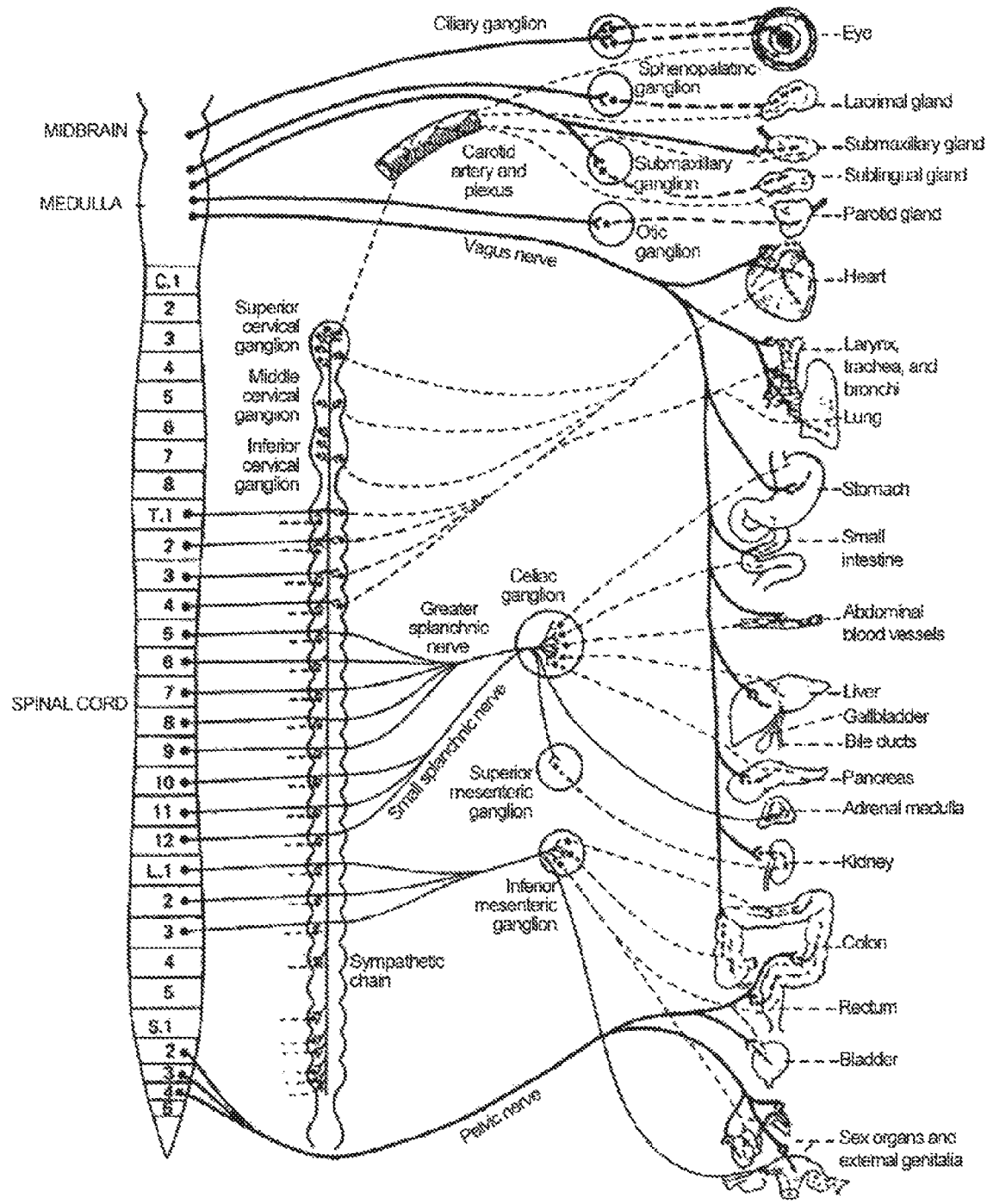
FIG. 1 is an anatomic representation of the supply of autonomic nerves to the organs of the human body.

The preset disclosure provides minimally invasive devices and methods to ablate nerves of the cardiopulmonary plexus and particularly deep cardiac plexus (DCP) for treating cardiopulmonary disease such as ventricular arrhythmias, pulmonary hypertension, or heart failure.

The present disclosure relates to a medical apparatus and method that offers treatment of cardiopulmonary disease such as ventricular arrhythmias, pulmonary hypertension, or heart disease. This treatment is provided through ablation of at least a portion of the nerves that comprise the deep cardiac plexus to impede or stop communication of a nerve signal along the ablated nerves, which can affect physiological responses that may be directly or indirectly involved in numerous factors of cardio-pulmonary health.

One preferred embodiment is a treatment apparatus comprising a device delivered through a patient's airway to the tracheal bifurcation. The treatment apparatus may comprise a mechanism to determine an optimal location on the wall of the trachea to penetrate for access to the target neural structures (e.g., deep cardiac plexus); a mechanism to penetrate the wall of the trachea; a method to confirm proximity to the nerve target; an ablation device that includes an ablation element (e.g., RF electrodes, cryogenic applicator, chemical agent delivery needle, ultrasound transducer, laser emitter); a mechanism to deliver and confirm safe and clinically effective ablation. The ablation device may be part of a treatment apparatus comprising other components that contribute to the functions of the apparatus or method of treatment. For example, the treatment apparatus may comprise an ablation energy source (e.g. RF signal generator, cryo console, ultrasound signal generator, chemical agent source or pump, laser generator), a controller, and a user interface. To ablate a portion of the targeted neural structure, the ablation energy source delivers ablation energy from an ablation element to the target neural structure. The treatment apparatus may be configured to position the ablation element, orient the direction of ablation energy delivery, and secure the position and orientation of the ablation element in order to safely and effectively deliver ablation energy to the target neural structure. To confirm that the positioning and orientation of the ablation element is adequate for safe and effective ablation of the target, for example proximity to the target, an agent, such as an electrical field or a drug, may be delivered to temporarily activate or block nerve activity and a physiological response may be observed or monitored for correlation to the nerve stimulation or block. Similarly, success of target neural structure ablation may be confirmed by electrical stimulation of the target nerve and observing the physiological response, changes in the physiological response compared to pre-ablation or absence of physiological response where one is expected. Physiologic response may comprise for example, refractory period of the heart, heart rate variability, heart rate, or blood pressure. A safety confirmation step may be done to confirm ablation energy will not be delivered to important non-target structures prior to delivery of ablation energy. For example, a safety confirmation step may comprise neural stimulation or blocking, tissue impedance measurement, or delivery of radiopaque contrast solution.

FIG. 1 is an anatomical representation of the supply of the autonomic nervous system to organs of the human body. The sympathetic and parasympathetic nervous systems comprise the autonomic nervous system.

The sympathetic nervous system (SNS) activates what is termed the fight or flight response. Like other parts of the nervous system, the SNS operates through a series of interconnected neurons. Sympathetic neurons are frequently considered part of the peripheral nervous system, although there are many that lie within the central nervous system (CNS).

Sympathetic neurons of the spinal cord, which is part of the CNS, communicate with peripheral sympathetic neurons via a series of sympathetic ganglia. Within the ganglia, spinal cord sympathetic neurons join peripheral neurons through chemical synapses. Spinal cord sympathetic neurons are therefore called presynaptic or preganglionic neurons, while peripheral sympathetic neurons are called postsynaptic or postganglionic neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (also referred to as norepinephrine). Prolonged activation can elicit the release of adrenaline from the adrenal medulla. Once released, noradrenaline and adrenaline bind adrenergic receptors on peripheral tissues. Binding to adrenergic receptors causes the effects seen during the fight-or-flight response. These include pupil dilation, increased sweating, increased heart rate, and increased blood pressure.

Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have thoracolumbar outflow. The deep cardiac plexus is formed by sympathetic postganglionic neurons that arise from the cervical ganglions with contributions from the ganglions between T1-T4.

The parasympathetic nervous system is responsible for the stimulation of rest-and-digest activities that occur when the body is at rest. Its action is described as being complimentary to that of the SNS (fight-or-flight). Nerve fibers of the parasympathetic nervous system (PNS) arise from the central nervous system. The parasympathetic preganglionic component has a supraspinal and spinal portion. Parasympathetic preganglionic neurons are found in four parasympathetic brain stem nuclei: nucleus Edinger-Westphal, superior salivatory nucleus, inferior salivatory nucleus, and the dorsal vagal complex of the medulla. Their axons exit via cranial nerves 3 (oculomotor); 7 (facial nerve); 9 (glossopharyngeal nerve); and 10 (vagus nerve), respectively. Parasympathetic preganglionic neurons are also found in the intermediolateral cell column of the sacral spinal cord in segments S2-S4 and exit the central nervous system via the sacral ventral roots and the spinal nerves and then continue to the pelvic viscera as the pelvic nerve. The deep cardiac plexus is innervated by the vagus nerve.

Figure 2:
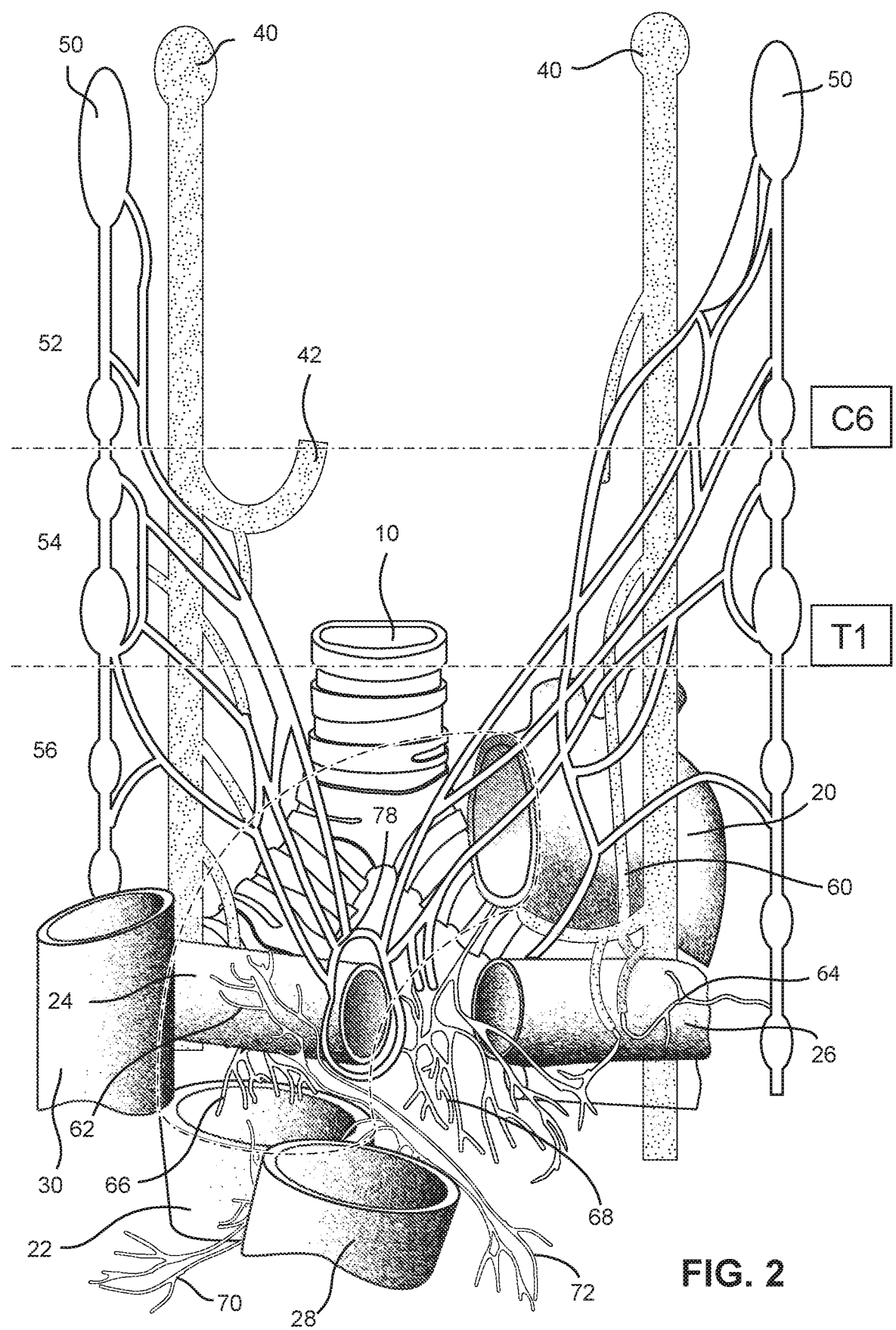
FIG. 2 is an illustration of the sympathetic and parasympathetic innervation of the cardiac and pulmonary plexus.

FIG. 2 is a schematic representation of the superficial cardiac plexus 78 and pulmonary plexus 62 and 64. The spinal segments are noted on the diagram as landmarks where C6 denotes the $6^{th}$ cervical segment and T1 the first thoracic segment of the spine (corresponding cervical and thoracic vertebrae). The cardiac muscle and pulmonary vascular beds are innervated by sympathetic and parasympathetic nerves. The vagus nerve 40, which is the $10^{th}$ cranial nerve, consists of a right and left vagus. The recurrent laryngeal nerve 42 is a branch of the vagus nerve that supplies the muscles of the larynx. There are two recurrent laryngeal nerves that emerge from the vagus nerve at the level of the aortic arch 20 and then travel up the sides of the trachea 10 to the larynx (not shown). The sympathetic trunk 50 is shown to illustrate the sympathetic cardiac nerves. The cervical cardiac branches 52 include contributions from the sympathetic ganglia above C6. The cervicothoracic cardiac branches 54 (a.k.a. mid-cervical/stellate ganglion) include contributions from the sympathetic ganglia between C6 and T1. The thoracic cardiac branches 56 include contributions from the sympathetic ganglia at T1 and below. The sympathetic nerves arise from the stellate (mid-cervical ganglia) 54 and upper thoracic ganglia 56 while parasympathetic innervation arises from the vagus nerve 40 to faun the cardiac plexus (CP). The CP is situated at the base of the heart and is divided into a superficial portion 78 and a deep portion 80 (shown in FIG. 3A and FIG. 3B). In FIG. 2 the heart is dissected to illustrate the origins of the CP and its relationship to the surrounding vasculature. The superior vena cava 30, pulmonary trunk 28, and aorta 22 are shown to illustrate the dissection of the heart from the schematic representation. The superficial CP 78 is situated below the aortic arch 20 and anterior to the right pulmonary artery 24. It is formed by the nerves from the right cervical cardiac branches 52, right and left cervicothoracic cardiac branches 56 and the cardiac branches of the cardiac vagus 44 (see FIG. 3B). The superficial cardiac plexus includes the cardiac ganglion that sends branches to the deep cardiac plexus 80 (shown in FIGS. 3A and 3B), the right cardiac plexus and the anterior left pulmonary plexus 64. The autonomic plexuses are illustrated in this schematic diagram. The right pulmonary plexus 62, supplying the right pulmonary artery 24, and left pulmonary plexus 64, supplying the left pulmonary artery 26, are formed by pulmonary branches of the vagus and the sympathetic trunk. The diagram also illustrates the right atrial 66, left atrial 68, right coronary 70 and left coronary 72 plexuses, respectively.

The target tissue where the DCP resides lies inside the larger area of the body called mediastinum. The mediastinum is a space in thoracic cavity between the lungs. Superior mediastinum contains the trachea, esophagus, arch of the aorta, thoracic portions of the left common carotid and the left subclavian arteries, innominate veins and the upper half of the superior vena cava, left highest intercostal vein, thymus, phrenic and vagus nerves and left recurrent nerves, thoracic duct and some lymph glands. The mediastinum is located in the middle of the thorax and is generally accessed by invasive surgery for medical intervention. Mediastinotomy is surgical opening of the mediastinum. A somewhat less invasive technique is called mediastinoscopy and performed using a type of an endoscope called mediastinoscope. During mediastinoscopy an incision is made in the suprasternal notch, and the soft tissue of the neck is bluntly dissected down to the trachea and distally to the carina. A mediastinoscope is inserted into the space allowing access to the paratracheal or tracheobronchial areas. As proposed in the present disclosure, identifying, accessing and targeting a small but vitally important area of paratracheal mediastinum that contains the deep cardiac plexus via a natural orifice such as the trachea is significantly less invasive and therefore is strongly desired. It is further desired to safely deliver energy and ablate the deep cardiac plexus to treat cardiac arrhythmias or pulmonary hypertension. Furthermore, the deep cardiac plexus location is not suitable for endovascular access and ablation that was proposed previously for sympathetic nerves located on the surface of pulmonary arteries. While less invasive than surgery, the transtracheal approach presents challenges of precise positioning and safety to surrounding tissues that were not previously resolved and were successfully addressed by the approach of the present disclosure.

Figure 3A:
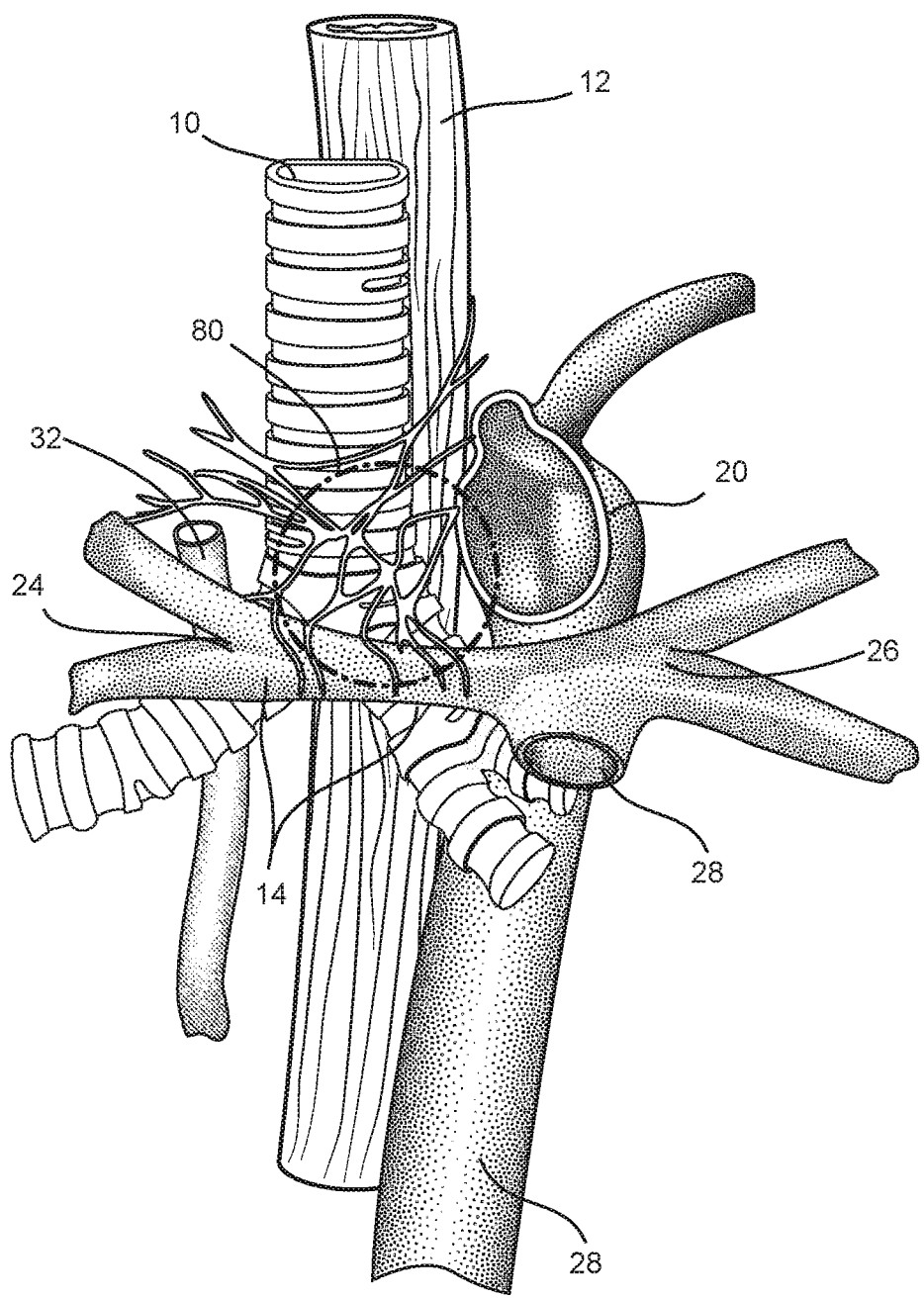
FIG. 3A is an illustration of the deep cardiac plexus and its anatomic location with relation to the trachea, aorta, and pulmonary arteries.
Figure 3B:
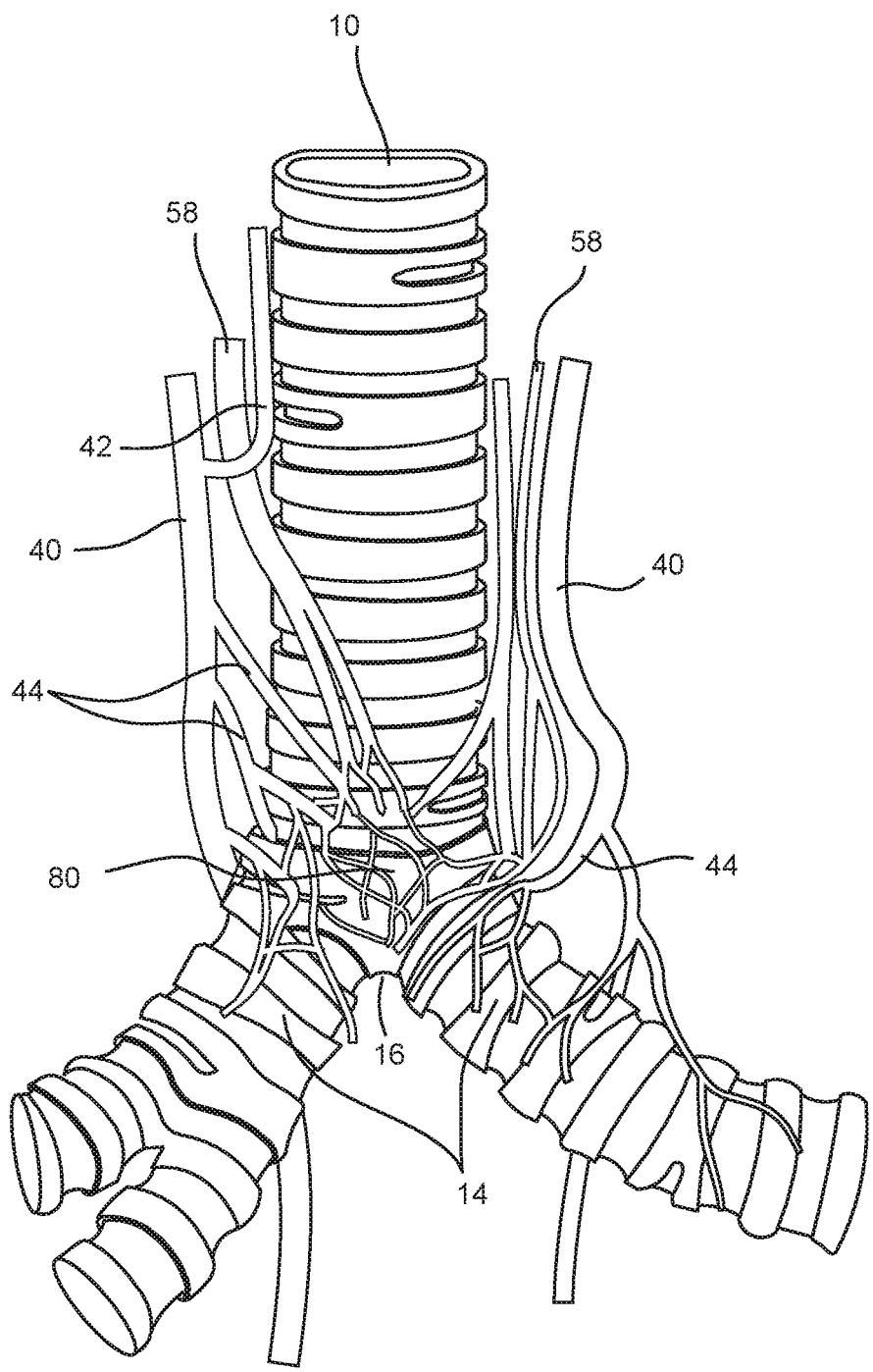
FIG. 3B is an illustration of the parasympathetic and sympathetic innervation of the deep cardiac plexus and its relationship to the trachea.

FIGS. 3A and 3B provide a schematic representation of the deep cardiac plexus 80 with (FIG. 3A) and without (FIG. 3B) the surrounding structures and vasculature. The deep cardiac plexus (DCP) 80 is located anterior to the tracheal bifurcation 16, just superior to the pulmonary division (24 and 26); and posterior to the aortic arch 20. The deep cardiac plexus 80 is formed by the sympathetic branches of the cervical ganglions 58 and branches of the vagus nerve 44 and recurrent laryngeal nerve 42. The only cardiac nerves which do not enter into the formation of the DCP are the superior cardiac nerve of the left sympathetic trunk and the lower of the two superior cervical cardiac branches from the left vagus nerve, which pass to the superficial part of the plexus 78. The branches from the right half of the DCP 80 pass, some anterior to, and others posterior to, the right pulmonary artery 24. The nerves that pass anterior to the pulmonary artery innervate the anterior pulmonary plexus and then form part of the anterior coronary plexus. The nerves that pass posterior to the pulmonary artery innervate the right atrium and then form part of the posterior coronary plexus. The left half of the DCP 80 is connected with the superficial cardiac plexus 78 and innervates the left atrium, the anterior pulmonary plexus and then forms the greater part of the posterior coronary plexus.

Central to the pathogenesis of PH is severe pulmonary artery vasoconstriction and elevated vascular resistance. Although endothelium derived Nitric Oxide (NO) is implicated in regulating pulmonary vascular tone, recent studies have highlighted the role of sympathetic nerve mediated vasoconstriction in the pulmonary arterial bed. Excessive sympathetic nerve activity with altered sympatho-vagal balance is frequently reported in PH and adversely affects prognosis. Sympathetic nerves from the lower cervical 54 and thoracic 56 sympathetic ganglia form the DCP 80 located anterior to the tracheal bifurcation 16. Pulmonary nerves from the DCP 80 travel anteriorly and innervate the main pulmonary arteries. The inventors have developed a minimally invasive method to identify, stimulate, and ablate the selected pulmonary sympathetic nerves at their origin at the DCP via a trans-tracheal approach.

In some embodiments the present disclosure provides a method of modulating activity of at least one sympathetic nerve, nerve fiber or neuron innervating the DCP 80 to ameliorate pulmonary hypertension. In some embodiments, the method includes advancing an intra-tracheal treatment apparatus to a target location close to or in close proximity to the tracheal bifurcation 16 of the patient; and using the treatment apparatus to modulate activity of at least one sympathetic nerve, nerve fiber or neuron innervating the DCP 80.

Currently, thoracic sympathectomy is performed surgically under general anesthesia via a bilateral thoracoscopic approach and is contraindicated in severe lung disease and in severe PAH, as such has limited utility in people who need this the most. Catheter ablation of the main pulmonary artery to destroy sympathetic nerves has been performed in a handful of patients with encouraging results, however, this requires significant expertise and is associated with severe endothelial injury to the pulmonary artery. Sympathetic nerves from bilateral sympathetic ganglia converge to form the DCP and this structure is consistently located in front of the tracheal bifurcation in humans (FIGS. 3A-3B). The inventors have developed a minimally-invasive method of accessing the DCP exploiting the anatomic relationship of the plexus to the tracheal bifurcation.

Figure 4A:
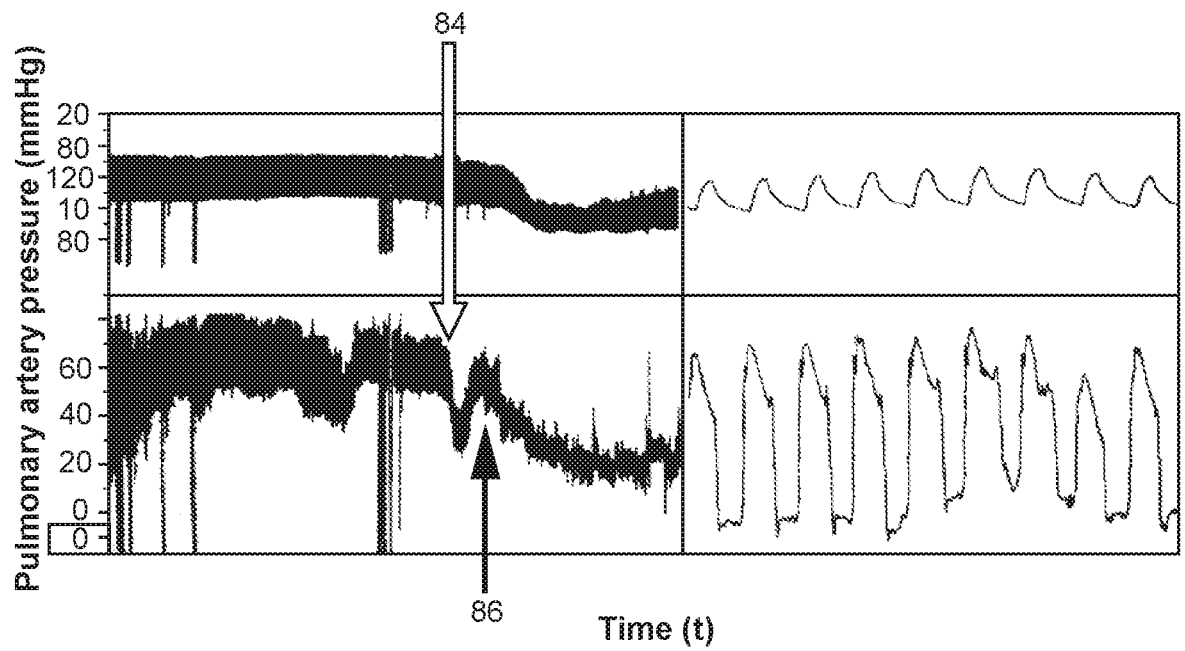
FIG. 4A illustrates physiological responses to a temporary block of the deep cardiac plexus in an experiment suggesting therapeutic effect on pulmonary hypertension.

Stimulation of the nerves of the cardiac plexus causes an increase in catecholaminergic responses such as tachycardia, increase force of contraction and pulmonary vasoconstriction. Stimulation also results in increased cardiac excitability and cardiac arrhythmias. Suppression of the nerve activating the DCP causes pulmonary vasodilation and reduction in cardiac arrhythmias. FIG. 4A illustrates a physiological response to a temporary block 84 and permanent ablation of nerves in the DCP. In an animal study, endobrachial ultrasound (EBUS) was used to visualize the tracheal bifurcation and the anterior tracheal space was accessed using a long 16 Gauge needle. In this example an electrode catheter was advanced through the needle into the mediastinal space after confirming the needle position based on EBUS and fluoroscopic imaging. Pulmonary, left ventricular and aortic blood pressures were measured by Millar brand diagnostic pressure monitoring catheters placed in the pulmonary artery, left ventricle and aorta respectively. Electrical stimulation was applied through the multipolar catheter and individually applied through the multiple bipolar electrodes in the mediastinal space. The specifications of the electrical stimulation signal were 20 Hz, 5V, 100 micro sec pulse width, and 1-5 mA. The physiological effect of electric stimulation, local administration of lidocaine, a short-acting nerve blocking chemical, and alcohol, a neurolytic substance injections on pulmonary blood pressure is shown in the plot of FIG. 4A. The thick arrow 84 indicates that the administration of lidocaine resulted in a dramatic drop in pulmonary artery pressure that recovered after 15 minutes. After returning to the baseline value, alcohol (ETOH) was injected into the deep cardiac plexus at a time indicated by the thin arrow 86. Alcohol ablation resulted in a >30 mmHg reduction in pulmonary artery pressure. The use of local administration of lidocaine or other suitable local anesthetic and the temporary reduction in pulmonary artery pressures can be used as a means of identification of the target location for administration of ablation therapy. The use of alcohol is an example of one substance that can be used to suppress nerve activity and provide reduction of pulmonary artery pressure.

In some embodiments, the treatment system 100 targets the elements of the nervous system which provide communication between the brain and the heart and pulmonary vasculature using electrical and chemical signals. A network of nerve tissue of the autonomic nervous system senses and regulates activity of the cardiovascular system. PH is characterized by increased circulating catecholamine levels, abnormally high muscle sympathetic nerve activity, and impaired heart rate variability, hallmarks of the systemic activation of central sympathetic tone. The innervation of the pulmonary artery is predominately sympathetic. The pulmonary artery receives innervation from the DCP. The treatment system 100 targets the sympathetic nerves of the DCP 80 to decrease the activity of at least one sympathetic neuron innervating at least the heart and at least one blood vessel of the pulmonary vasculature. In some embodiments, reducing pulmonary vascular resistance may involve ameliorating PH. FIG. 4A Illustrates the reduction of pulmonary artery pressure in response to both a temporary and a permanent block of the nerves in the DCP. The 30 mmHg reduction is indicative of a clinically relevant treatment for PH.

Figure 4B:
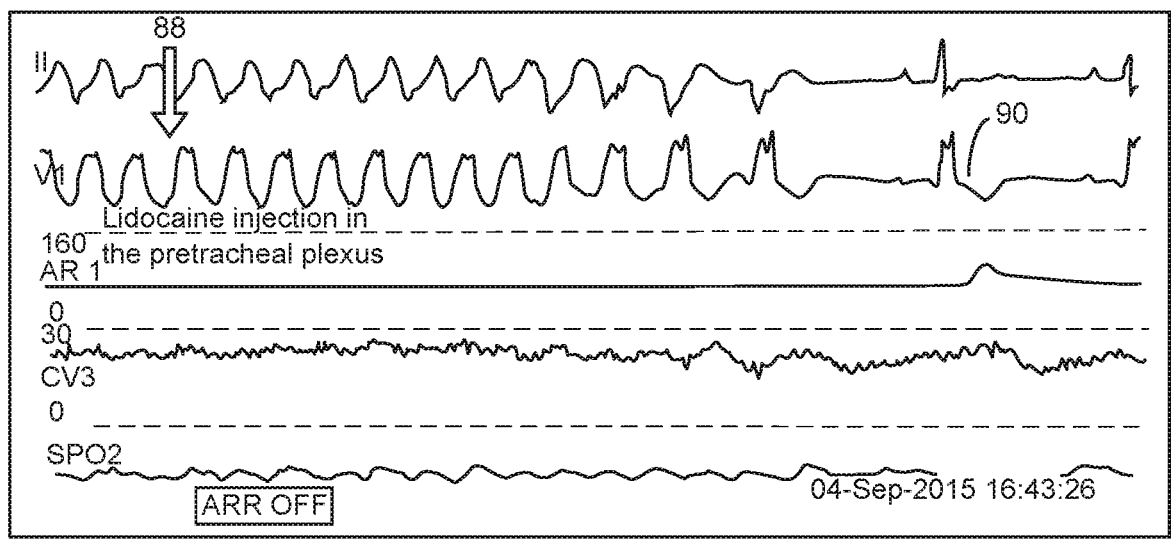
FIG. 4B illustrates physiological responses to a temporary block of the deep cardiac plexus in an experiment suggesting therapeutic effect on ventricular arrhythmia.

FIG. 4B shows physiological monitoring plots during an experiment by the inventors on a human subject. The patient had incessant ventricular tachycardia during the initial period as shown by the electrocardiogram (ECG) prior to the arrow 88. The injection of lidocaine was performed without invasive surgery, with a long needle that was introduced through the airway of the patient, punctured the tracheal wall at the location of the DCP and entered the mediastinal space. The needle positioning and puncture was guided by an EBUS equipped bronchoscope in order to confirm the puncture cite and the position of the needle tip and to avoid major blood vessels. The arrow 88 indicates an injection of lidocaine into the DCP to temporarily block nerve signals. Following the arrow 88, ventricular tachycardia slows down to a regular paced rhythm 90. This experiment confirms that temporary interruption of the DCP can stabilize a patient's heart demonstrating tachycardia, suggesting that permanent disruption of the DCP via neural ablation may eliminate ventricular arrhythmia in some patients. It also confirms viability of accessing DCP non-invasively from the trachea and feasibility of ultrasound imaging for the safety of the procedure.

Other methods of ablation for the suppression of nerve activity are disclosed herein. There are several accepted methods of ablating a nerve or a plexus once it is accessed including RF ablation using resistive heating, cryo-ablation using cold, ultrasound heating ablation and injection of neurolytic blocking agents (e.g., a form of nerve block involving deliberate injury of a nerve by the application of a chemical, in which case the procedure is called neurolysis) in which a chemical such as alcohol or a more specifically acting sympatholytic agents such as guanethidine, botox (i.e., botulium toxin A) and others may be applicable.

Figure 5:
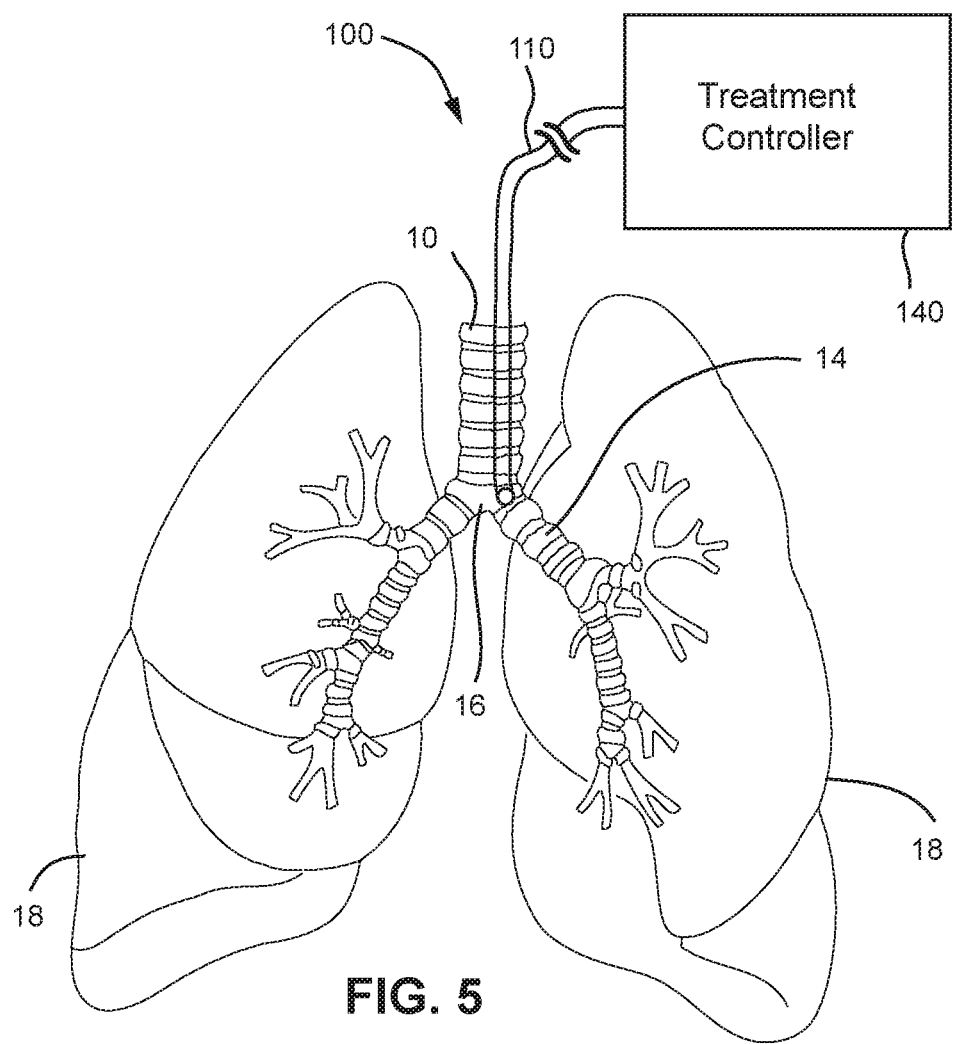
FIG. 5 is a schematic view of a treatment apparatus positioned in the trachea at the tracheal bifurcation.
Figure 9:
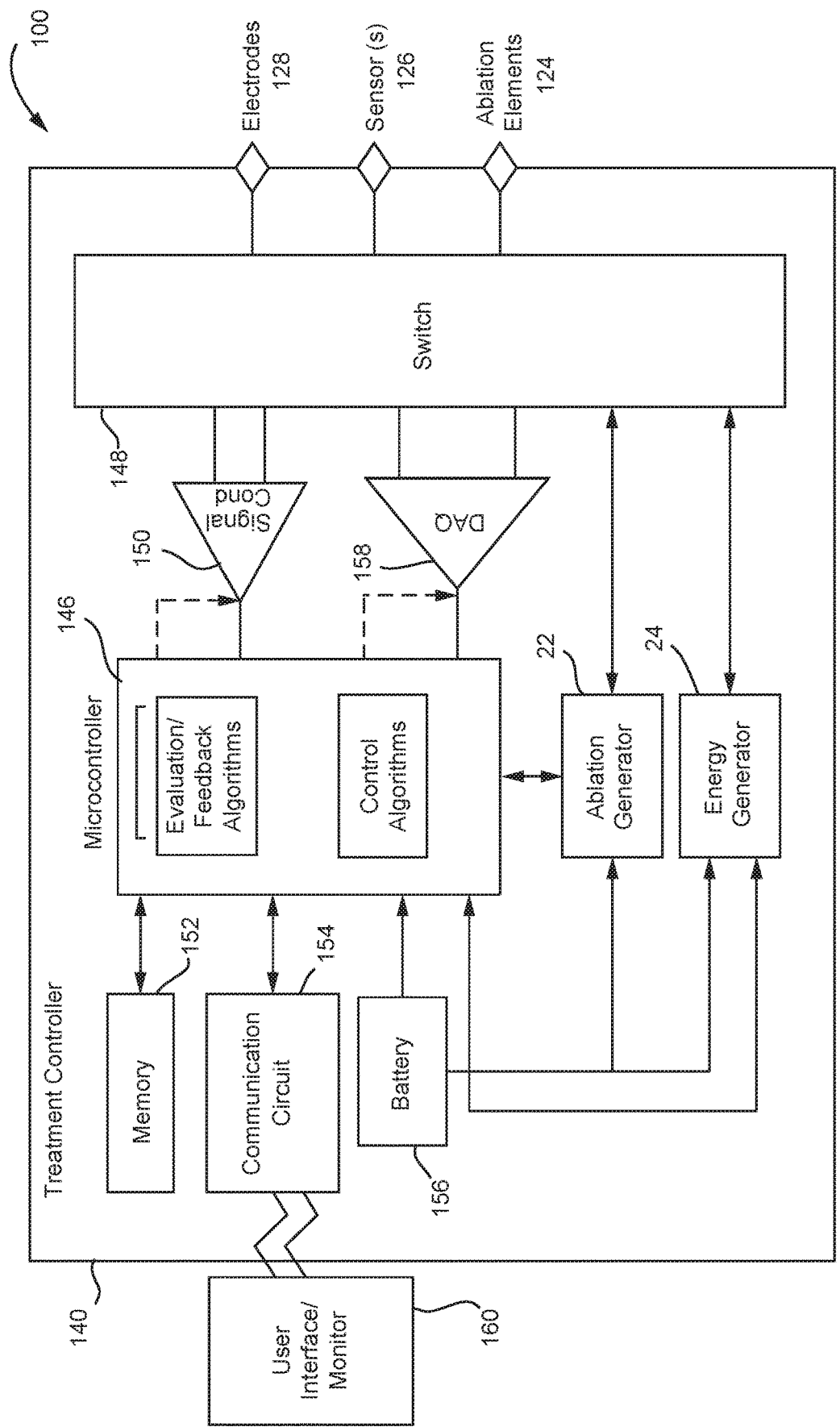
FIG. 9 is a functional diagram of a treatment system.

In some embodiments the treatment system 100 as shown in FIG. 5 and FIG. 9 includes a treatment controller 140 which is connected to a treatment apparatus 110. The treatment apparatus 110 is advanced into the body of a patient through the airway. The treatment apparatus 110 is advanced close to or in close proximity to the tracheal bifurcation 16 and used to modulate the activity of at least one sympathetic nerve or nerve fiber or neuron innervating the DCP 80. A mechanism to visualize the location of the device within the airway in relation to the airway walls, in relation to bone landmarks and in relation to main blood vessels outside of these walls may be used to confirm deployment of the apparatus in the desired location. Examples of visualization systems are EBUS and fluoroscopy. A treatment controller 140 may comprise a microcontroller 146 to control the function of the ablation generator 142, and user interface 160 that is connected to the treatment apparatus 110. The ablation generator 142 may emit energy, for example ablation energy selected from a group consisting of radiofrequency (monopolar, bipolar or other forms); ultrasound (high intensity focused, low frequency, other forms); microwave; light; heat; phototherapy; magnetic; electrical; electromagnetic; and cryotherapy.

The present disclosure provides an apparatus and method to access target nerves (e.g. CP, DCP) through the tracheal wall and modulate a function of one or more cardiac or pulmonary nerves to produce desired therapeutic results. The vascular tone of pulmonary vessels are in part controlled by the sympathetic ganglia via the pulmonary nerves. These nerves arise in the cervical and thoracic sympathetic ganglia and form a plexus called the DCP 80 in front of the tracheal bifurcation 16 (FIGS. 3A and 3B). Electrical stimulation of these nerves results in increase in pulmonary pressures. Conversely, blocking these nerves causes lowering of the pressure. The present apparatus and method exploits the unique anatomy of the cardiac plexus to easily access, ablate and achieve permanent disruption of unilateral or bilateral pulmonary nerves to achieve reduction in pulmonary arterial pressure in pulmonary hypertension.

Figure 6A:
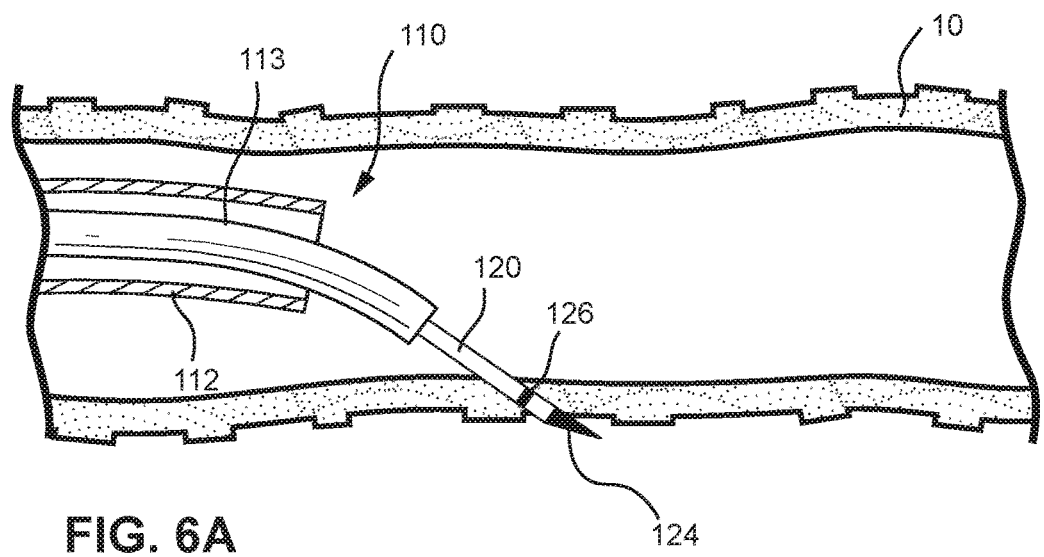
FIG. 6A is a cross-sectional view of a treatment apparatus extending out from a delivery assembly.
Figure 6B:
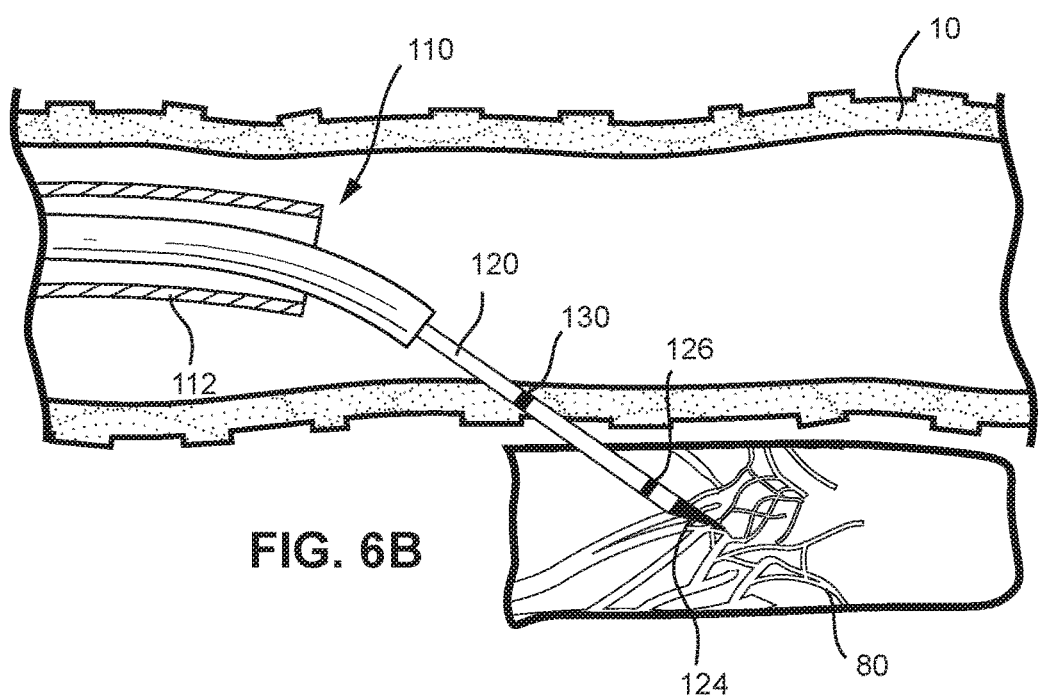
FIG. 6B is a view of a distal tip of the treatment apparatus in FIG. 6A positioned to affect target nerves.

FIG. 6A and FIG. 6B illustrate embodiments of a treatment apparatus positioned along an airway such as a trachea 10. The treatment apparatus is capable of transmitting ablative energy. The treatment apparatus 110 comprises an ablation device 120 that has a distal tip. The ablation device 120 extends through a working lumen of an airway device 112 and includes a flexible shaft and a deployable ablation device 120 protruding from the shaft. The ablation device 120 includes at least one ablation element 124. Ablation energy may be delivered from the ablation element 124 to target tissue. The ablation device 120 may comprise one or more ablation elements 124 and temperature sensors 126 that cooperate to provide localized delivery of energy to minimize, limit, or substantially eliminate unwanted ancillary trauma associated with the applied energy.

The ablation element 124 may be configured to output energy that ablates tissue. The terms "ablate" or "ablation", including derivatives thereof, include, without limitation, substantial altering of electrical properties, mechanical properties, chemical properties or other properties of tissue. The term element within the context of "ablation element" includes a discrete element, such as an electrode, or a plurality of discrete elements, such as a plurality of spaced apart electrodes, which are positioned so as to collectively treat a region of tissue or discrete sites. One embodiment of an ablation element 124 emits energy that ablates neural tissue when the element is coupled to and energized by an energy source 144. Examples of energy emitting ablation elements include, without limitation, electrode elements coupled to direct current (DC) sources or alternating current (AC) sources (e.g., radiofrequency, RF, current sources), antenna elements energizable by microwave energy sources, pulsed high voltage sources, heating elements (e.g., metallic elements or other thermal conductors which are energized to emit heat via convective heat transfer, conductive heat transfer, etc.), light emitting elements (e.g., fiber optics capable of transmitting light sufficient to ablate tissue when the fiber optics are coupled to a light source), light sources (e.g., lasers, light emitting diodes, etc.), ultrasonic elements such as ultrasound transducers adapted to emit ultrasound waves sufficient to ablate tissue when coupled to suitable excitation sources), combinations thereof and the like.

As used herein, the term "ablate," including variations thereof, is construed to include, without limitation, to destroy or to permanently damage, injure, or traumatize tissue. For example, ablation may include localized tissue destruction, cell lysis, cell size reduction, necrosis, or combinations thereof.

In some embodiments, the ablation device 120 may be connected to an energy generator 144 (e.g., RF) by electrical conductors within the shaft of the ablation device. For example, the RF electrical generator can be incorporated into the treatment controller. In some embodiments, the RF electrical generator may be incorporated into the ablation assembly. RF energy may be outputted to a desired frequency based on the treatment. Example frequencies include, without limitation, frequencies in the range of about 50 kHz to about 1000 MHz (e.g., 350 to 500 kHz). When the RF energy is directed into tissue, the energy is converted within the tissue into heat allowing the temperature of the tissue to be increased, for example to a range of 40° C. to about 99° C. In some embodiments, a temperature sensor 126 may be used to monitor the temperature of the target tissue (e.g., tissue containing a target neural structure such as a CP or DCP) to confirm therapeutic delivery of RF. A temperature sensor 130 may also be used to monitor temperature of non-target tissue (e.g., tracheal wall 10) to reduce or avoid iatrogenic injury. In some embodiments the RF generator may deliver 5 to 50W of RF energy. Other ranges of frequencies and power outputs can also be used.

A user can visually inspect the airway using the airway device 112 of FIGS. 6A and 6B to locate and evaluate treatment site(s) and non-targeted tissue before, during, and/or after performing therapy. The airway device 112 can be a catheter, delivery sheath, bronchoscope, endoscope, or other suitable device for guiding the treatment apparatus. In some embodiments, the airway device 112 includes at least one viewing device, such as an optical viewing device (e.g., camera), optical train (e.g. a set of lenses), and the like. For example, the airway device 112 can be in the form of a bronchoscope having one or more lights for illumination and optical fibers for transmitting images. By way of another example, an airway device 112 may comprise an ultrasound viewing device. The ultrasound viewing device may be connected to an operator display and capable of visualizing tissues of different density and blood flow using Doppler sonography.

FIG. 6A shows a distal end of a shaft of a treatment apparatus proximate to the wall of the trachea 10. The ablation device 120, that can have a sharp tip capable of penetrating the trachea 10, is deployed from the shaft and contacts the wall. As shown in FIG. 6B the ablation device 120 is then advanced through the tracheal wall until the exposed ablation element 124 is in close proximity to the target tissue (e.g., deep cardiac plexus 80). The position of the ablation device 120 can be adjusted by extending or retracting the ablation device 120. Because the ablation device 120 is relatively slender (e.g., between about 14 Ga to 22 Ga), the wall of the trachea may experience an insignificant amount of trauma. The ablation device 120 may include a temperature sensor 126 to monitor the temperature of the target tissue. At least one or more temperature sensors 130 can be located along the ablation device 120 and positioned in the wall of the trachea. The temperature in the wall of the trachea may be monitored to insure that harmful heating of the trachea does not occur. Generally, living human body tissues are not harmed by temperatures above body temperature and below 40° C. and can be ablated at temperatures above 50° C. Temperatures above 90° C. are typically avoided during RF ablation since they cause boiling of water in tissue, charring and impedance rise at electrodes with smaller tissue interface areas. Temperature monitoring is performed to optimize therapy in the target zone while protecting the non-target tissue. For example, the duration of energy delivery can be 60 sec and a temperature of 80° C. can be maintained at the electrode tissue interface using temperature feedback control.

In another embodiment, temperature sensors may be temporarily implanted in the wall of the trachea without being coupled to an ablation device 120. For example, a pair of temperature sensors may be implanted in the wall of the trachea. The pair of temperature sensors may be connected to a treatment controller 140 and the temperature of the trachea during ablation therapy may be monitored by the treatment controller 140 during therapy to maintain a safe temperature in the tracheal wall. Impedance measurements may be taken of the temperature sensors implanted in the tracheal wall to confirm placement within the tracheal wall prior to initiating ablation treatment.

An ablation device may comprise a sterility protective mechanism. The inner lumen 11 of a trachea is unsterile and caution may be taken to avoid infecting tissue during a treatment, for example while passing an ablation device from the inner lumen of the trachea through the tracheal wall to target tissue. To maintain sterility, an ablation device should not be repeatedly retracted and advanced back into the tissue during the procedure unless measures are taken to avoid contamination. For example, a protective sterile environment may be provided by the device design. Examples of sterilization techniques may include irrigation with an antiseptic fluid, UV light or other means to rapidly kill bacteria.

Figure 7:
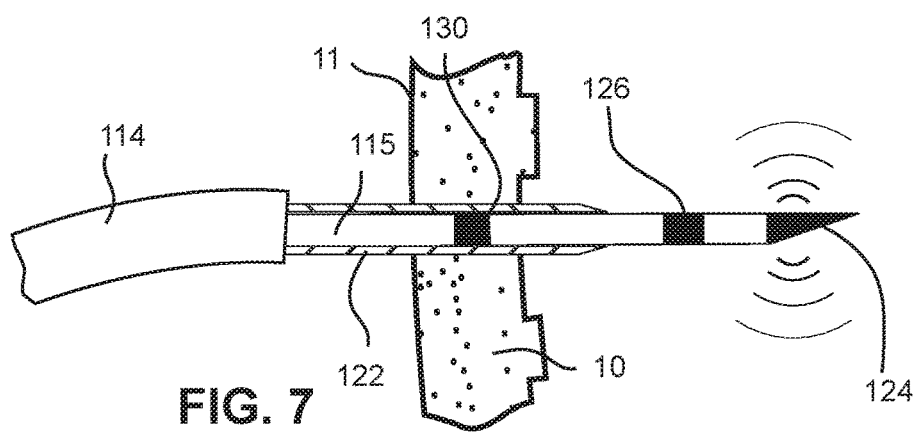
FIG. 7 is a schematic illustration of a treatment apparatus.

FIG. 7 illustrates an embodiment of an airway device 114 that provides a mechanism to maintain the protective sterile environment of an ablation device 115. A sterile sheath 122 allows for repeated retraction and advancement of the ablation device 115 from the inside to outside of the trachea as needed during the treatment while maintaining a sterile environment. The sterile sheath 122 may be advanced through the wall of the trachea and fixed in place during the introduction of the ablation device 115, delivery of ablation energy, and retraction of the ablation device.

In some embodiments Damage to surrounding structures, such as the aorta and pulmonary arteries may be limited by utilizing bipolar RF as an ablation energy, which localizes heating as well as the distance of the target (DCP) from the aorta and pulmonary arteries. Natural body functions can help prevent, reduce or limit damage to the non-target tissues. The aorta and PA have thick, muscular walls that seal if punctured with a relatively thin needle. Additionally, the blood within the aorta and pulmonary arteries can absorb the thermal energy and carry the energy away thus preventing thermal damage to the wall of the vessel. In this manner, thermal energy is transferred to the blood. Another embodiment for protecting the pulmonary artery comprises deploying a deployable structure such as an insulated balloon to create separation distance between the pulmonary arteries and the deep cardiac plexus during treatment. An increased separation distance may decrease the risk of ablative energy injuring the pulmonary arteries or other non-target tissue. The trachea, to the contrary, if poorly perfused and has no natural thermal protection by blood flow and it may be desired to implement a mechanism to protect the trachea from ablation energy in a device embodiment.

In some embodiments, a treatment apparatus 110 such as the embodiment shown in FIG. 6A, FIG. 6B, and FIG. 7 includes a stabilization mechanism. The device may be stabilized once the location for penetrating the wall of the trachea at the tracheal bifurcation is obtained. The device may be stabilized in the location using a deployable stabilization structure such as a deployable wire cage or balloon or a stabilizing method where the stabilizing portion is advanced into both bronchi. A stabilizing balloon may be filled with fluid to allow energy transmission. The fluid filled balloon may also act as a virtual electrode. The device shown in FIG. 6A and FIG. 6B may allow air to flow through or past the treatment apparatus while it is in the treatment configuration to allow ventilation of the lung tissue distal to the target location. For example, a stabilization mechanism (not shown) may be positioned around the airway device 112 in its distal region and a lumen 113 of the airway device 112 may provide passage of the treatment apparatus 110 as well as air. In another embodiment a stabilization mechanism may be configured to allow air to pass through it. For example, a stabilization mechanism may be a deployable cage comprising splines and voids between the deployed splines for passage of air.

Figure 8A:
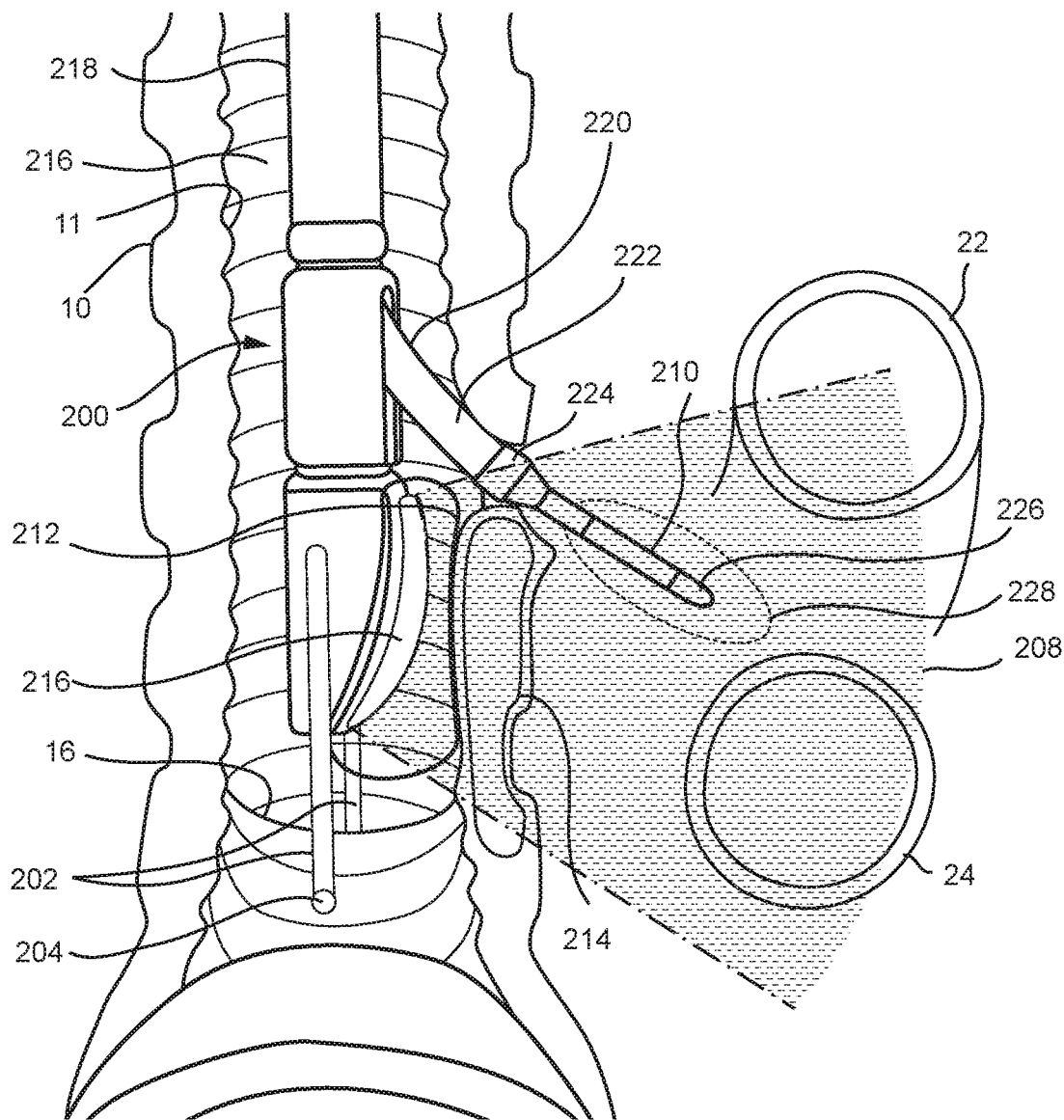
FIG. 8A and FIG. 8B is a schematic illustration of a treatment apparatus.

FIG. 8A is a cutaway illustration of an embodiment of a treatment apparatus 200 positioned in a patient's trachea 10. The distal end of the apparatus 200 is configured to couple with a tracheal bifurcation 16. For example, in this embodiment the apparatus 200 comprises two diverging arms 202 shown in FIG. 8A straddling the tracheal bifurcation. The function of coupling with the bifurcation may improve stability of the apparatus 200 during steps of imaging, targeting, confirming position relative to neural structures (e.g., using electrical stimulation or blocking) deploying an ablation element, delivering ablation energy, repositioning the ablation element, or confirming ablation. Coupling with the bifurcation may facilitate ease of use of the apparatus 200. For example, a user may insert the apparatus 200 into the patient's trachea (e.g. through and endotracheal tube) and when the arms 202 come into contact with the tracheal bifurcation tactile resistance may be felt. The arms 202 may comprise blunt distal tips 204 and be resiliently elastic so trauma to the inner lumen of the trachea 11 is avoided. The arms may be elastically retracted as the apparatus 200 is delivered through an endotracheal tube (not shown) and elastically deployed (e.g., to extend at a greater angle to the axis of the apparatus) when advanced beyond the endotracheal tube. In a deployed configuration the arms 202 may be spread apart sufficient to engage with the carina of the tracheal bifurcation yet not become lodged in the trachea during advancement.

The apparatus 200 further comprises at least one ultrasound imaging transducer 206 that may be used to image tissue in the vicinity of the target space. An imaging plane 208 may be used to detect anatomical landmarks such as the aorta 20 and right pulmonary artery 24, which may be used to guide delivery of an ablation element 210 to a target space while avoiding important non-target structures. For example, the ablation element may be delivered through the anterior wall of the trachea and extend a desired distance (e.g., in a range of about 3 mm to 20 mm) from the wall of the trachea, and cranial to the carina of the tracheal bifurcation (e.g., in a range of about 0 mm to 30 mm) and remain between the aorta 20 and right pulmonary artery 24. The ultrasound imaging transducer 206 may be in electrical communication with an ultrasound console (not shown) that delivers a controlled signal to the transducer and receives signals from the transducer that are echoed off of tissue in the imaging plane 208. The ultrasound console may comprise software that translates received signals in to an image that is displayed on a monitor. A balloon 212 may contain a medium (e.g., sterile water, saline) to transmit ultrasound waves. The balloon may further function to cool the tracheal wall. For example, the medium may be circulating through lumens (not shown) in the shaft of the apparatus 200 so the medium can absorb and remove heat from the tracheal wall, creating a protected region of the tracheal wall 214. Cooling the protected region 214 may avoid inadvertent heating and iatrogenic injury of the trachea that otherwise might be caused by delivering ablation energy.

The apparatus 200 may comprise a deployable stabilization mechanism 216 configured to hold the distal region of the apparatus still relative to the trachea once the distal region of the apparatus is positioned near the tracheal bifurcation 16. The stabilization mechanism 216 may be on an apparatus with arms 202 to act in combination with the arms to stabilize the distal region, or alternatively on an apparatus without arms 202. As shown the stabilization mechanism may be a deployable cage of strands that bow out radially in the deployed configuration to contact the trachea and center the shaft 218 of the apparatus in the trachea, while allowing air to pass through the trachea. Alternatively, a stabilization mechanism may position the shaft 218 within the trachea 10 towards the anterior aspect of the tracheal lumen. The stabilization mechanism may be self-deployed when the advanced beyond an endotracheal tube or sheath. For example, the stabilization mechanism 216 may be made of elastic material having shape memory. Alternatively a stabilization mechanism may be deployed by the user, for example by applying tension to a pull wire connected to the stabilization mechanism.

Figure 8B:
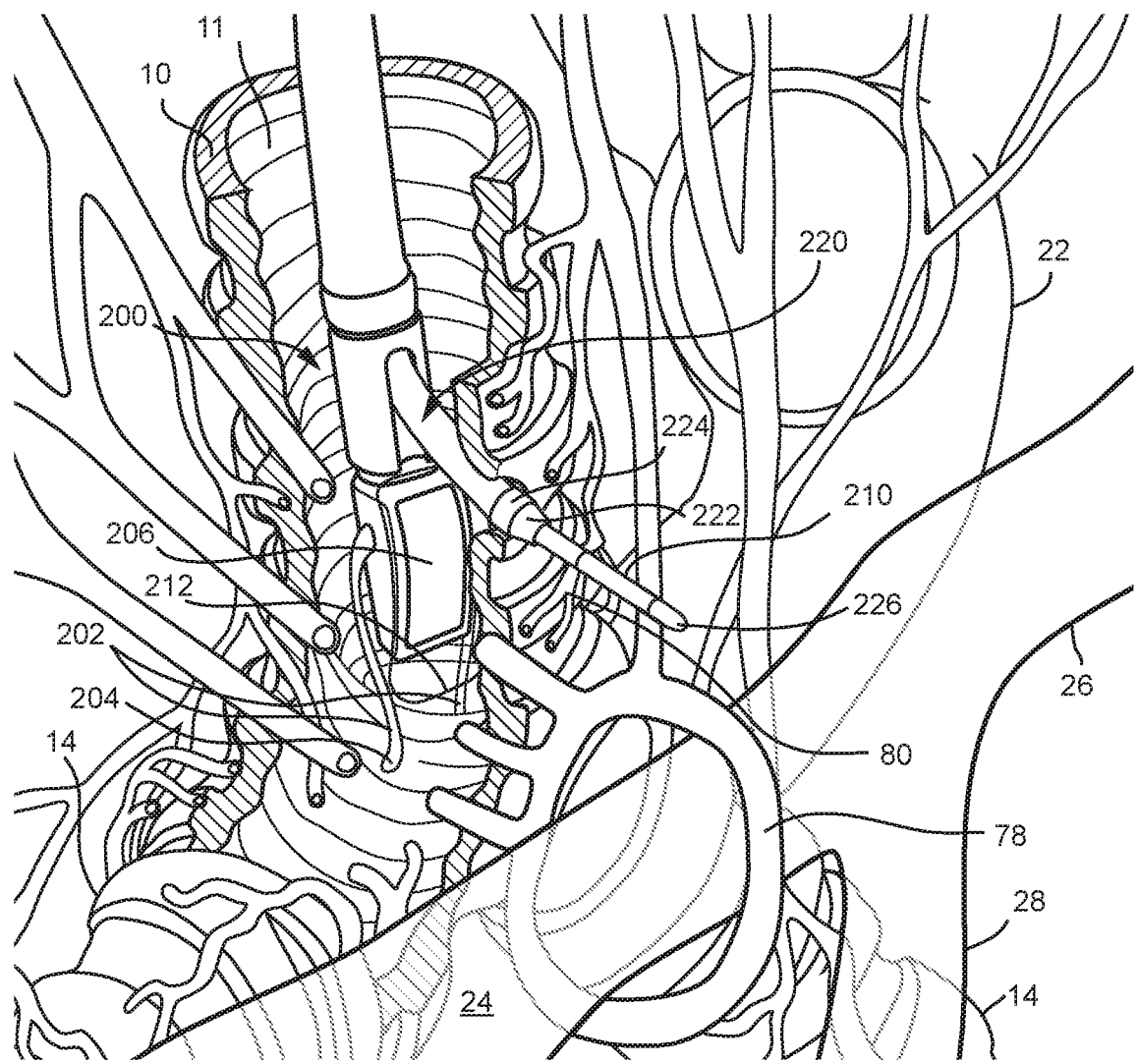

The apparatus 200 may comprise a deployable ablation probe 220 having an ablation element 210 that is retracted into the shaft 218 in an undeployed configuration and extends from the shaft in a deployed configuration as shown in FIG. 8A and FIG. 8B. Alternatively, an ablation probe may be on a separate catheter that is delivered through a lumen of the shaft 218. The ablation probe 220 may comprise a sterile sheath 222 that may be configured to puncture through the tracheal wall and provide a lumen through which an ablation element may be slidably engaged. The sheath 222 may comprise a temperature sensor 224 such as a thermocouple for placement in the tracheal wall to monitor temperature or control ablation energy delivery to ensure the tracheal wall remains at a safe temperature. The temperature sensor 224 may be positioned in a radiopaque band or echogenic marker that can be imaged (e.g., with fluoroscopy or ultrasound imaging). The temperature sensor 224 may be positioned on an impedance sensor used to measure tissue impedance, which may facilitate indication of being positioned in the tracheal wall. The ablation probe 220 may comprise an ablation element 210 such as a radiofrequency electrode as shown. Alternatively, an ablation element may be configured to deliver an alternate form of ablation energy such as a chemical agent through an injection port, or other forms of energy described herein. The ablation element 210 may be associated with an imaging marker (e.g., radiopaque marker, echogenic marker) that allows the position of the ablation element relative to anatomical structures to be identified. Tissue impedance may be measured in association with the ablation element providing indication of type of tissue the element 210 is contacting. The distal tip 226 of the ablation probe may be blunt as shown allowing passage through soft tissue while avoiding puncturing of the aorta 20 or pulmonary artery 24. A tissue ablation zone 228 surrounds the ablation element 210. The ablation element and ablation energy may be configured to create an ablation zone sufficient to disrupt target neural tissue while remaining contained in a desired target space to avoid undesired injury of nearby structures such as the trachea, aorta and pulmonary artery. FIG. 8B shows an isometric view of the apparatus 200 positioned in a trachea 10 with an ablation element 210 deployed for selective ablation of a deep cardiac plexus 80 or superficial cardiac plexus 78.

A schematic of and embodiment of a treatment system 100 is shown in FIG. 9, which shows various components of the treatment system 100. The system includes a treatment controller 140 (also shown in FIG. 5). The treatment controller 140 may comprise an ablation generator 142 (e.g., cryo console, chemical agent source or pump), an energy generator 144 (e.g., electrical stimulation source, RF signal generator, ultrasound signal generator, laser generator), and a microcontroller 146 with embedded logic and software. The treatment controller 140 may be in communication with a user interface 160 with controls and displays. The microcontroller 146 includes a microprocessor (or other control circuitry), RAM or ROM memory, logic and timing circuitry, state machine circuitry, and I/O circuitry. The programmable microcontroller 146 controls various operations of the treatment controller 140 including physiological monitoring, ablation therapy, tissue temperature monitoring, and electrical nerve stimulation. A treatment apparatus such as the treatment apparatus 110 shown in FIG. 6A and FIG. 6B) may be connected to the treatment controller 140 and may comprise an airway device 112 that facilitates the positioning of an ablation device 120 that includes at least one ablation element 124 to deliver ablation therapy and at least one temperature sensor 126 and 130 to monitor the temperature of tissue to improve performance and safety of the ablation system. Additional elements such as electrodes 128 (electrical stimulation elements) can be added to confirm the technical and/or clinical success of the ablation therapy. Stimulation of nerves may be achieved by the application of low frequency, low energy electric current that is not ablative, for example in the 10-30 Hz, 1-10 mA range. Physiologic sensors 126 may be connected to the treatment controller 140. The physiologic sensors may be used to confirm the technical or clinical success of the ablation therapy. The signal conditioning circuitry 150 may be selectively coupled to physiologic sensors 126 through the switch 148. The signal conditioning circuitry 150 may include dedicated sense amplifiers, multiplexed amplifiers, or shared amplifiers. Each sensing circuit may employ one or more low power precision amplifiers with programmable gain or automatic gain control, bandpass filtering, or a threshold detection circuit to sense the physiologic parameter of interest.

In some embodiments the ablation element 124 may be an RF electrode (e.g., having an exposed surface area of 5 to 15 mm$^2$) in monopolar configuration with a dispersive grounding pad on the patient's skin to complete the electrical circuit. In other embodiments, the configuration of the RF electrode may be bipolar. Ablation energy may be radiofrequency electrical current having a frequency in a range of about 350 to 500 kHz and a power in a range of about 5 to 50 W. The delivery of RF energy may be controlled by an energy generator 144 associated with a treatment controller 140 that uses temperature feedback from a sensor associated with the RF electrode. In some embodiments the ablation element 124 functions to emit a substance as an ablation agent. In such embodiments the system may further comprise a means to inject the substance such as a manually operated syringe or automatically controlled pump. The emitted substance may be selected from a group consisting of saline, phenol, ethanol, botulinum toxin or other neurotoxins, anesthetic agent, including but not limited to depolarizing or non-depolarizing agents, such as Marcaine, bupivacaine, lidocaine, or other anesthetic agents, and other agents capable of reducing nerve signal transmission.

In some embodiments deployment of a treatment apparatus to the tracheal bifurcation 16 may be assisted with the use of a camera for visualization. Upon confirming location at the tracheal bifurcation 16, imaging ultrasound (e.g. positioned on an airway device) may be used to identify a location for penetrating the tracheal wall 10 which may increase safety by avoiding puncturing of blood vessels and may improve efficacy by visually identifying a target zone or anatomical landmarks for example. Once the ablation device 120 has penetrated the wall, electrical stimulation may be used to confirm proximity to the target neural structure (e.g. DCP). Physiological responses may be monitored to verify the identification of the DCP 80. In some embodiments, deployment of the treatment apparatus to the tracheal bifurcation 16 is performed under fluoroscopic guidance.

The treatment apparatus 110 exploits the unique anatomy of the cardiac plexus to easily access, ablate and achieve permanent disruption of bilateral pulmonary nerves to achieve a therapeutic effect in treating cardiopulmonary disease. In some embodiments, an airway device includes a reusable ultrasound probe/workstation and a single-use mapping and ablation catheter. The present disclosure provides an ablation device 120 to deactivate or ablate at least one sympathetic nerve, nerve fiber or neuron innervating the DCP 80. The airway device may include an elongated tubular structure equipped with an ultrasound transducer at its distal end and at least one, two or more additional lumens, a needle (e.g., ablation device 120) at the distal end that is advanceable through the lumen having at least one ablation element (e.g. RF ablation element 124) that can be advanced in close proximity of at least one of the nerves innervating the DCP 80.

Figure 10:
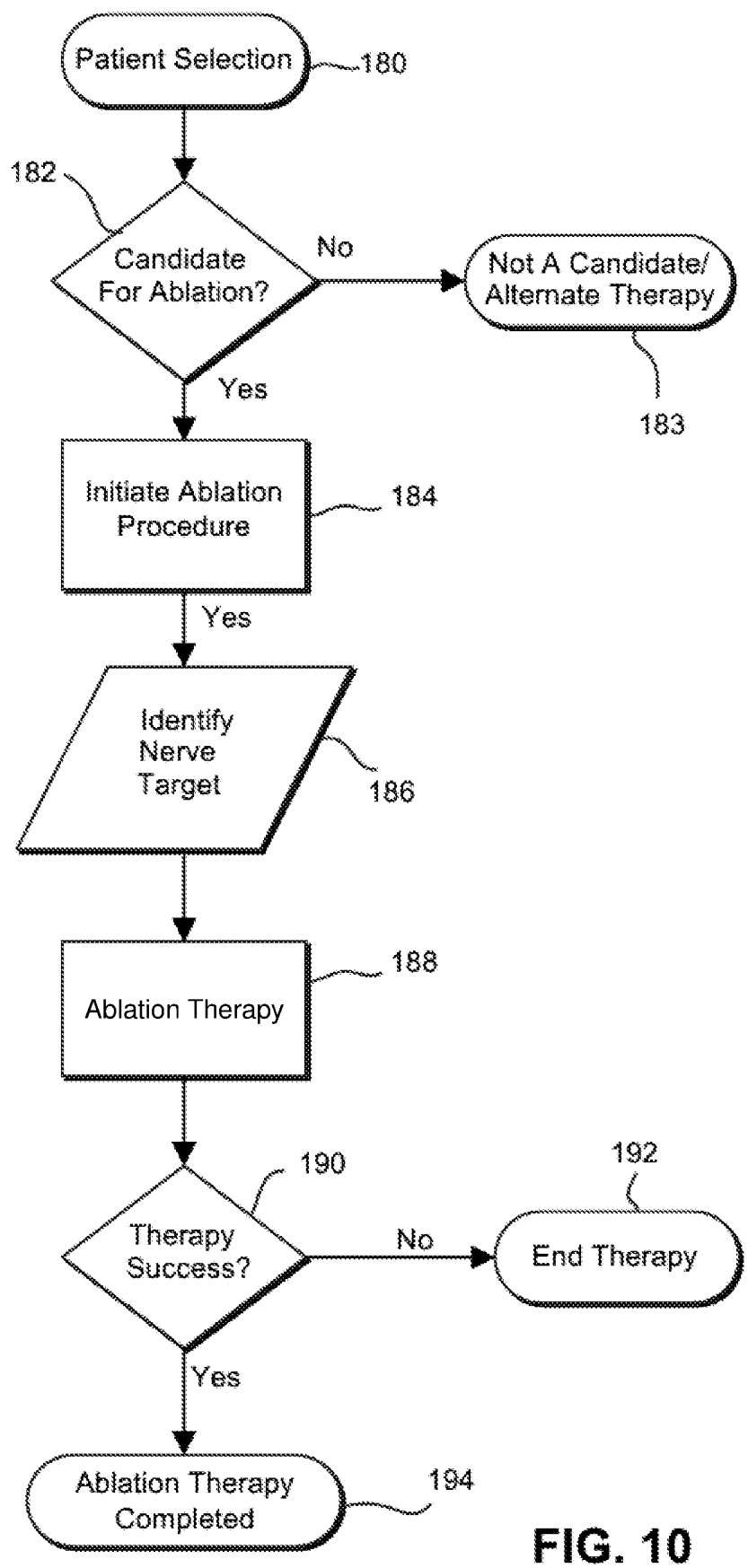
FIG. 10 is a flowchart illustrating steps from patient selection to ablation therapy.

FIG. 10 is a flowchart illustrating a method for the treatment of PH from patient selection 180 to successful ablation therapy delivery 194. Prior to administering ablation therapy for the treatment of PH, a determination of a patient as a candidate for ablation therapy 182 may be made. One means for determining suitability is to produce a temporary block of the nerves innervating the DCP. One means of temporary block of the nerves innervating the DCP is local administration of lidocaine. A drop in pulmonary artery pressure correlated to a temporary block may be indicative of a patient's suitability for ablation therapy. Other physiological measures may be used to assess suitability for treatment and success of treatment after the ablation depending on the condition of the patient and treatment goals. Various cardiac indexes have been proposed to reflect autonomic activity including heart rate variability (HRV), heart rate recovery after exercise (HRR) and QT-interval. A decrease in the low frequency component of HRV (LF-HRV) and/or a shortening of the QT-interval is indicative of a decrease in cardiac sympathetic tone, indicating successful block of the DCP. If the temporary block is not successful, the patient is not a candidate for ablation and other suitable therapeutic interventions may be pursued. Initiation of the ablation procedure may occur for patients determined to be candidates for ablation of the deep cardiac plexus. Comparing physiologic measurements before and after the treatment may inform the physician of the success of the treatment or indicate a need to repeat it.

The ablation procedure 184 starts by positioning the treatment apparatus into the airway of the patient (as shown in FIG. 5). The treatment apparatus 110 may be introduced into the airway via the mouth or nose of the patient. The treatment apparatus 110 may comprise an airway device 112, which includes instruments for visualization, positioning, and delivering the ablation device 120. The distal region of the airway device 112 is positioned at the tracheal bifurcation. The airway device 112 is introduced to provide visualization to confirm desired positioning and may be performed using a miniature video camera, sonography, fluoroscopy, or other means. A stabilization means may also be implemented to maintain position during the ablation procedure. One example of a stabilization means would be the use of a balloon. The airway device 112 and/or stabilization means may be configured to maintain airflow throughout the airway during the procedure. After the airway device 112 is properly positioned, the sharp ablation device 120 may be used to penetrate the trachea to position the ablation device 120 to be in close proximity to the target neural structure (DCP 80). In some embodiments, airway device 112 may include an ultrasound imaging probe configured to generate an ultrasound image to identify anatomical landmarks that indicate relative position of a target ablation zone. For example, a position of a target ablation zone comprising a patient's DCP may be identified by a space of tissue bordered by the anterior wall of the trachea proximate a tracheal bifurcation, the aorta and the left pulmonary artery. The ultrasound imaging probe may be used to identify non-target tissues posing a safety risk such as blood vessels prior to penetration of the trachea to avoid vessel puncture and bleeding. Ultrasound imaging may be performed prior to deploying an ablation probe or penetrating the tracheal wall, during delivery of an ablation probe or penetration of the tracheal wall, during delivery of ablation energy, or following delivery of ablation energy.

Prior to penetrating the tracheal wall, a local anesthetic may be applied by the treatment apparatus to the tracheal wall to improve patient comfort. For example the local anesthetic may be delivered through a lumen of the ablation probe and sprayed on the tracheal wall. An antiseptic may be applied to the tracheal wall prior to penetration to reduce a risk of infection. For example the antiseptic may be delivered through a lumen of the ablation probe and sprayed on the tracheal wall.

In some embodiments the ablation elements 124 as well as all of the structures of the ablation device 120 that are positioned outside of the trachea are sterile. To maintain sterility, a mechanism may be included in the airway device 112 to prevent repeated reinsertion after retraction of the ablation device 120 back into the trachea. Maintaining sterility during the ablation procedure helps to reduce the probability of infection. After successful ablation occurs, the ablation device 120 may be retracted back into the trachea.

Identification of the nerve target 186 may be performed by using electrical stimulation of the nerves and monitoring the physiological response. Electrical stimulation of the DCP 80 may result in an increase in pulmonary vascular resistance that may be evaluated by monitoring pulmonary artery pressure. Another means of identification of the nerve target could be providing a temporary block of the nerves innervating the DCP 80. A temporary block could be performed by injection of lidocaine. Another means of temporary block could be high frequency (e.g., 3-10 kHz) electrical AC stimulation to limit neural transmission in the DCP. Identification of the nerve target may be performed using a deployable structure, such as a deployable ablation probe further configured for identification of the nerve target. For example, the ablation probe may comprise a stimulation electrode, which may be the same or a different electrode than the ablation element in the case of using an RF electrode as an ablation element. A lumen in the deployable ablation probe may be used to deliver injection of a temporary block. Following confirmation of target identification, ablation therapy may be initiated.

In some embodiments, the ablation therapy 188 is RF electrical energy. RF energy provides ablation of the target nerves by heating the tissue. To maintain a safe temperature and protect non-target tissues from damage, temperature sensors 126 may be used to monitor the temperature and provide feedback to the treatment controller 140. Temperature may be monitored adjacent to the ablation element 124 to monitor the temperature of the target nerve tissue (T=40-99° C.). Additionally, a temperature sensor or sensors 126 may be positioned in non-target tissues to prevent damage of non-target tissue (T<40° C.). Physiological sensors 126 may be used to evaluate therapy success 190. For example, a reduction of pulmonary artery pressure may be used to confirm therapy success.

Another means of evaluating therapy success may be to monitor the physiological response to stellate ganglion (middle cervical ganglion) stimulation. The stellate ganglion block is commonly performed by anesthesiologist or pain specialist to treat pain and involves inserting a needle through skin and deeper tissues. It is most commonly done at C6 level as this level provides well defined landmarks and relative safety against inadvertent intravascular injection. These techniques are known. The inventors also performed endovascular stellate ganglion block using blood vessels to access and introduce the needle into the stellate ganglion. The intravascular access to the per-vascular location and the physiologic responses to of right stellate ganglion (RSG) and left stellate ganglion (LSG) stimulation are understood. The inventors conducted an experiment in which the right and left stellate ganglia were accessed and electrically stimulated with an EP catheter from inside of the adjacent blood vessel. Navigation was performed using fluoroscopy and known anatomic landmarks. Right stellate ganglion stimulation resulted in doubling of resting heart rate and blood pressure with a significant increase in LV pressure and LV dP/dt. Left stellate ganglion stimulation resulted in predominant increase in LV pressure and LV dP/dt. Frequent ventricular arrhythmias were noted during LSG stimulation. Injection of lidocaine in the pretracheal space containing the deep cardiac plexus abolished these responses during the temporary neural blocking effect of the lidocaine. Stellate ganglion stimulation that can be endovascular (trans-arterial or trans-venous) can be incorporated in the DCP ablation procedure to confirm the successful ablation and interruption of neural pathways to the heart. Prior to initiation of ablation therapy, stimulation of the stellate ganglion could be performed and the physiological response recorded via the data acquisition system 158 of the treatment controller 140 (FIG. 8). After completion of the ablation therapy, the stellate ganglion may be stimulated to compare the physiological response to the response recorded prior to ablation therapy. A physiological response to electrical stimulation of the stellate ganglion following DCP ablation that is decreased or eliminated compared to the response to stimulation before DCP ablation may be a quick and reliable indication that the DCP was ablated sufficiently to create a desired therapeutic effect and the ablation therapy may be considered a success 194. If the post DCP ablation response is the same or similar to the pre-ablation response, ablation therapy may be repeated until a successful outcome is achieved or the therapy session may be ended 192. In the event that an acute test of therapeutic success results are negative, which may indicate that the DCP was not sufficiently ablated, an ablation may be performed again. The treatment controller 140 may comprise a software algorithm to analyze the previous ablation. For example, the algorithm may consider ablation energy delivery parameters and inputs from sensors that may suggest a reason for an unsuccessful ablation such as movement of an ablation element, disruption of energy delivery, or inability to deliver a desired quantity of ablation energy to the target location. The algorithm may generate an error message or suggestions to the user for how to repeat an ablation. The following ablation may be done in a different location within the target ablation area, or with greater ablation energy for example to ablate the DCP or a greater portion of the DCP. Following the second ablation evaluation of therapy success may be repeated. If the evaluation 190 is positive the ablation therapy may be completed 194 and the ablation element may be withdrawn from the tissue and tracheal wall and the treatment apparatus may be removed from the patient's trachea. If the evaluation 190 is negative ablation may be repeated until success is reached.

Another embodiment for confirming ablation of the deep cardiac plexus may comprise inducing ventricular arrhythmias, for example by electrically stimulating a stellate ganglion, prior to ablation to identify a stimulation threshold. Following ablation, ventricular arrhythmia may be induced again and if greater stimulation is required to induce arrhythmia, i.e., if a threshold for induction of ventricular arrhythmia is increased, a successful DCP ablation may be confirmed.

In another embodiment electrophysiological (EP) testing may be used to evaluate therapy success. EP testing involves the recording of local myocardial activity and stimulation of myocardial tissue using electrode catheters. Programmed electrical stimulation (programmed stimulation rates) is used to induce arrhythmias that mimic the rate and morphology of the spontaneous arrhythmia being treated by ablation therapy. EP testing may be performed prior to ablation therapy to confirm the ability to induce the spontaneous arrhythmia in a clinical setting. To assess therapy success after ablation therapy is initiated, EP testing may be performed to assess inducibility of the arrhythmia. An inability to induce the arrhythmia may be an indicator of therapy success. Other known indications of sympathetic stimulation of the heart can be used to confirm cardiac denervation including the length of refractory period and heart rate variability.

Clinical success of the ablation therapy may be measured by assessing improvements in clinical parameters, such as exercise capacity, as well as evaluation of the patient's HRQoL. Exercise testing consists of either a 6-minute walk test or a cardiopulmonary exercise test. Additionally, a patient's HRQoL may be assessed by administering a standardized HRQoL questionnaire such as the SF-36. While at least one exemplary embodiment of the present invention(s) is disclosed herein, it should be understood that modifications, substitutions and alternatives may be apparent to one of ordinary skill in the art and can be made without departing from the scope of this disclosure.

This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. References to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the invention, the preferred methods and materials are now described.

EXAMPLES

1. A method of modulating activity of at least one sympathetic nerve, nerve fiber or neuron innervating the deep cardiac plexus to ameliorate pulmonary hypertension the method comprising: advancing an treatment apparatus to a target location close to or in close proximity to the tracheal bifurcation of the patient; and using the treatment apparatus to modulate activity of at least one sympathetic nerve, nerve fiber or neuron innervating the deep cardiac plexus.

2. A method as in example 1, wherein the advancement of the treatment apparatus comprises advancing an ablation device that emits energy selected from the group consisting of monopolar radiofrequency, bipolar radiofrequency, other forms of radiofrequency, high intensity focused ultrasound, low frequency ultrasound, other forms of ultrasound, microwave, light, heat, cold radiation, phototherapy, magnetic, electrical, electromagnetic, cryotherapy, plasma, mechanical, and chemical, and wherein using the treatment apparatus comprises emitting energy from the ablation element.

3. A method as in example 1, wherein the advancement of the ablation device comprises advancing a substance emitting ablation device, and wherein using the ablation device comprises emitting a substance from the ablation element.

4. A method as in example 3, wherein the emitted substance is selected from the group consisting of saline, phenol, ethanol, vincristine, an antineoplastic drug, botulinum toxin, other neurotoxins, anesthetic agents, depolarizing agents, non-depolarizing agents, marcaine, bupivacaine, lidocaine, or other anesthetic agents, and other agents capable of reducing nerve signal transmission.

5. A method as in example 3, further comprising, before emitting the substance, advancing at least one ablation element out of the ablation device, wherein the substance is emitted out of the at least one ablation element.

6. A method as in example 1, further comprising, after the advancement of the ablation device, penetrating through the wall of the trachea to enter the anterior or inferior space under the trachea to deliver the ablation treatment.

7. A method as in example 1, wherein the airway device is stabilized in the location using a balloon or a stabilizing method including a method where the device bifurcates and advances into both bronchi for stability.

8. A method as in example 7, wherein the balloon can be filled with fluid to allow energy transmission or act as a virtual electrode.

9. A method as in example 1, further comprising allowing air to flow through or past the airway device while it is in the treatment configuration, to allow ventilation of lung tissue distal to the target location.

10. A method as in example 1, wherein ameliorating pulmonary hypertension comprises decreasing pulmonary vascular resistance in at least one artery of the pulmonary vasculature.

11. A method of reducing pulmonary vascular resistance comprises decreasing activity of at least one sympathetic neuron innervating at least one blood vessel of the pulmonary vasculature.

What is claimed is:

1. A method for ablating a deep cardiac plexus of a patient, the method comprising:
   advancing a treatment apparatus into a trachea of the patient,
   extending an ablative energy delivery element of the treatment apparatus through a wall of the trachea at a level of the trachea proximate a tracheal bifurcation by penetrating the wall of the trachea, wherein the penetration includes puncturing and traversing the wall of the trachea,
   positioning the ablative energy delivery element at a target space, wherein the positioning is performed via a visualization system of the treatment apparatus within the trachea and the target space is identified by an anterior wall of the trachea proximate the tracheal bifurcation, an aorta and a left pulmonary artery, and
   ablating, by the ablative energy delivery element, tissue within the target space to substantially disable the deep cardiac plexus.

2. The method of claim 1, wherein the positioning includes ultrasonically imaging the target space from within the trachea.

3. The method of claim 1, further comprising coupling a distal region of the treatment apparatus to the tracheal bifurcation.

4. The method of claim 1, further comprising monitoring tissue temperature during the ablating and controlling the ablating based on the tissue temperature.

5. The method of claim 4, wherein the monitored tissue temperature corresponds to tissue of the wall of the trachea.

6. The method of claim 1, further comprising thermally protecting the wall of the trachea during the ablating of the tissue.

7. The method of claim 6, wherein the thermally protecting the wall of the trachea comprises circulating cooling fluid in thermal communication with the wall of the trachea.

8. The method of claim 1, wherein the positioning of the ablative energy delivery element comprises electrical nerve stimulation and measuring physiologic responses.

9. The method of claim 1, wherein the positioning of the ablative energy delivery element comprises placing the ablative energy delivery element in the tissue within the target space, wherein the tissue within the target space is within 3 to 20 mm anterior and 0 to 30 mm cranial of a saddle of a carina of the tracheal bifurcation and between the aorta and the left pulmonary artery.

10. The method of claim 1, further comprising applying electrical stimulation and measuring physiologic responses after the ablating.

11. The method of claim 8, wherein the measuring of the physiologic responses comprises measuring refractory period of a heart, heart rate variability, heart rate, or blood pressure.

12. The method of claim 1, wherein the ablating of the tissue within the target space disables the deep cardiac plexus resulting in reduced ventricular arrhythmia.

13. The method of claim 1, wherein the ablating of the tissue within the target space disables the deep cardiac plexus resulting in reduced heart rate.

14. The method of claim 1, wherein the ablating of the tissue within the target space disables the deep cardiac plexus resulting in reduced pulmonary vascular resistance.

15. The method of claim 1, wherein the ablating of tissue within the target space disables the deep cardiac plexus resulting in reduced pulmonary blood pressure.

16. The method of claim 1, wherein the ablating of the tissue within the target space disables the deep cardiac plexus resulting in reduced efferent sympathetic innervation of a heart of the patient.

17. The method of claim 1, further comprising confirming ablation of the deep cardiac plexus by measuring a reduction of response to stimulation of a stellate ganglion compared to a response to stimulation of the stellate ganglion prior to the ablating.

18. The method of claim 1, further comprising confirming ablation of the deep cardiac plexus by measuring a substantial increase of a threshold for induction of ventricular arrhythmias.

19. A method of treating a cardiopulmonary disease comprising:
   selecting a patient diagnosed with cardiac arrhythmias,
   advancing a treatment apparatus into a trachea of the patient to a tracheal bifurcation,
   positioning an ablation element of the treatment apparatus at a target space, wherein the positioning is performed via a visualization system of the treatment apparatus within the trachea and the target space identified by an anterior wall of the trachea proximate the tracheal bifurcation, an aorta and a left pulmonary artery,
   penetrating the anterior wall of the trachea to extend the ablation element,
   delivering ablation energy from the ablation element of the treatment apparatus through the anterior wall of the trachea to tissue comprising a deep cardiac plexus, wherein the ablation energy disrupts neural signals from the deep cardiac plexus, and
   removing the treatment apparatus from the patient.

20. The method of claim 19, wherein the delivering of the ablation energy from the treatment apparatus through the anterior wall of the trachea further comprises:
   penetrating the anterior wall of the trachea 3 to 20 mm superior to the tracheal bifurcation,
   positioning the ablation element of the treatment apparatus into the tissue comprising the deep cardiac plexus, and
   applying the ablation energy from the ablation element of the treatment apparatus to the tissue.

21. The method of claim 19, wherein the tissue comprising the deep cardiac plexus comprises a space in mediastinum defined by an anterior wall of the trachea, the aorta and the left pulmonary artery.

22. The method of claim 19, wherein the cardiopulmonary disease is ventricular arrhythmia, cardiac arrhythmia, atrial arrhythmia, pulmonary hypertension, pulmonary vascular resistance, or heart failure.

23. The method of claim 19, wherein the ablation energy disrupts the neural signals from the deep cardiac plexus resulting in a decrease in pulmonary vascular resistance, improved health, decreased dyspnea or increased exercise capacity.

24. The method of claim 19, further comprising confirming the ablation energy will be delivered to the deep cardiac plexus by delivering a temporary nerve block to the tissue and evaluation of HRV, QT-interval, or pulmonary arterial pressure.

25. The method of claim 19, further comprising confirming that the ablation energy disrupts the neural signals from the deep cardiac plexus by electrically stimulating a stellate ganglion before and following the delivery of the ablation energy and measuring an improvement in HRV, QT-interval or pulmonary arterial pressure following the delivery of the ablation energy compared to before the delivery of the ablation energy.

26. A method of treating a patient comprising:
   selecting a patient with cardiac arrhythmias,
   advancing and positioning an ablation device inside a trachea of the patient at a level of a bifurcation saddle of the trachea, wherein the positioning the ablation device is performed via a visualization system within the trachea and the ablation device is positioned at a target tissue space identified by an anterior wall of the trachea proximate a tracheal bifurcation, an aorta and a left pulmonary artery,
   advancing an ablation element of the ablation device though a wall of the trachea, wherein advancing the ablation element comprises puncturing the anterior wall of the trachea, and
   delivering ablation energy from the ablation element to the target tissue space wherein the ablation energy ablates at least a portion of a deep cardiac plexus,
   wherein the ablation of at least a portion of the deep cardiac plexus results in a therapeutic effect selected from a list comprising reducing sympathetic stimulation of a heart of the patient, reducing cardiac arrhythmias, reducing pulmonary hypertension, improving HRQoL, and relieving dyspnea.

27. The method of claim 26, further comprising imaging tissue in a region of the target tissue space to guide the positioning of the ablation device or the advancing of the ablation element or the delivery of the ablation energy.

28. The method of claim 26, further comprising delivering a stimulation to elicit a physiological response to confirm that the delivery of the ablation energy from the ablation element will be delivered to the target tissue space.

29. The method of claim 26, further comprising injecting radiopaque contrast under fluoroscopy or ultrasound imaging to avoid injury of a non-target tissue such as the aorta or a pulmonary vein.

30. The method of claim 26, wherein the cardiac arrhythmias of the patient comprise ventricular arrhythmias.

31. The method of claim 26, wherein the cardiac arrhythmias are refractory to drug and surgical cardiac arrhythmia ablation therapy.

32. The method of claim 26, wherein the patient with cardiac arrhythmias is also receiving surgical and catheter cardiac arrhythmia ablation therapy.

33. The method of claim 26, further comprising coupling the ablation device to an inner surface of the bifurcation saddle of the trachea.

34. The method of claim 26, wherein the target tissue space is pretracheal space in a mediastinum of the patient defined by the trachea, the aorta and the left pulmonary artery.

35. The method of claim 27, wherein imaging tissue comprises endotracheal ultrasonic imaging, computer tomography, fluoroscopy, or bronchoscopy.

36. The method of claim 26, further comprising thermally protecting the tracheal wall from the ablation energy.

37. The method of claim 36, wherein the thermally protecting of the tracheal wall comprises:
   positioning a cooling mechanism of the ablation device in thermal communication with the tracheal wall proximate to the target tissue space,
   monitoring temperature of the tracheal wall, and
   controlling the delivery of the ablation energy at least in part based on the monitoring of the temperature of the tracheal wall.

* * * * *